(12) United States Patent
Tsai

(10) Patent No.: US 8,748,011 B2
(45) Date of Patent: Jun. 10, 2014

(54) RUTHENIUM CARBENE COMPLEXES FOR OLED MATERIAL

(75) Inventor: Jui-Yi Tsai, Newtown, PA (US)

(73) Assignee: Universal Display Corporation, Ewing, NJ (US)

( * ) Notice: Subject to any disclaimer, the term of this patent is extended or adjusted under 35 U.S.C. 154(b) by 479 days.

(21) Appl. No.: 13/033,229

(22) Filed: Feb. 23, 2011

(65) Prior Publication Data

US 2012/0212125 A1 Aug. 23, 2012

(51) Int. Cl.
*H01L 51/54* (2006.01)
*C09K 11/06* (2006.01)

(52) U.S. Cl.
USPC ........... 428/690; 428/917; 313/504; 313/506; 252/301.16; 257/40; 257/E51.044; 548/103; 548/108

(58) Field of Classification Search
None
See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Hager et al. "Charge-transfer exited states of ruthenium(II) complexes. I. Quantum yield and decay measurements." J. Am. Chem. Soc. 1975. vol. 97, No. 24, p. 7031-7037.*

(Continued)

*Primary Examiner* — Michael H Wilson
(74) *Attorney, Agent, or Firm* — Duane Morris LLP

(57) ABSTRACT

Neutral ruthenium(II) complexes having at least one bidentate carbene coordinated to the ruthenium through a ruthenium-carbene bond are provided. Also provided are organic light emitting devices comprising the ruthenium(II) carbene complexes.

28 Claims, 3 Drawing Sheets

Formula I

(56) References Cited

U.S. PATENT DOCUMENTS

| | | |
|---|---|---|
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0214576 A1* | 9/2005 | Lamansky et al. ............ 428/690 |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0114174 A1 | 5/2008 | Wei et al. |
| 2008/0124572 A1 | 5/2008 | Mizuki et al. |
| 2008/0220265 A1 | 9/2008 | Xia et al. |
| 2008/0297670 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0092854 A1 | 4/2009 | Walters et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0115322 A1 | 5/2009 | Walters et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 10/2009 |
| WO | WO 01039234 | 5/2001 |
| WO | WO 02002714 | 1/2002 |
| WO | WO 0215645 | 2/2002 |
| WO | WO 03040257 | 5/2003 |
| WO | WO 03060956 | 7/2003 |
| WO | WO 2004093207 | 10/2004 |
| WO | WO 2004107822 | 12/2004 |
| WO | WO 2005014551 | 2/2005 |
| WO | WO 2005/019373 | 3/2005 |
| WO | WO 2005019373 | 3/2005 |
| WO | WO 2005030900 | 4/2005 |
| WO | WO 2005089025 | 9/2005 |
| WO | WO 2005123873 | 12/2005 |
| WO | WO 2006009024 | 1/2006 |
| WO | WO 2006/018292 | 2/2006 |
| WO | WO 2006056418 | 6/2006 |
| WO | WO 2006072002 | 7/2006 |
| WO | WO 2006082742 | 8/2006 |
| WO | WO 2006098120 | 9/2006 |
| WO | WO 2006100298 | 9/2006 |
| WO | WO 2006103874 | 10/2006 |
| WO | WO 2006114966 | 11/2006 |
| WO | WO 2006132173 | 12/2006 |
| WO | WO 2007002683 | 1/2007 |
| WO | WO 2007004380 | 1/2007 |
| WO | WO 2007063754 | 6/2007 |
| WO | WO 2007063796 | 6/2007 |
| WO | WO 2008101842 | 8/2008 |
| WO | WO 2008132085 | 11/2008 |
| WO | WO 209000673 | 12/2008 |
| WO | WO 2009003898 | 1/2009 |
| WO | WO 2009008311 | 1/2009 |
| WO | WO 2009018009 | 2/2009 |
| WO | WO 2009/046266 | 4/2009 |
| WO | WO 2009050290 | 4/2009 |
| WO | WO 09066778 | 5/2009 |
| WO | WO 2008056746 | 5/2009 |
| WO | WO 2009021126 | 5/2009 |
| WO | WO 2009062578 | 5/2009 |
| WO | WO 2009063833 | 5/2009 |
| WO | WO 2009066779 | 5/2009 |
| WO | WO 2009086028 | 7/2009 |
| WO | WO 2009100991 | 8/2009 |

OTHER PUBLICATIONS

Chen et al., "Strategic design and synthesis of novel tridentate bipyridine pyrazolate coupled Ru(II) complexes to achieve superior solar conversion efficiency" Journal of Materials Chemistry, J. Mater. Chem., 2009, 19, 5329-5335, Dec. 19, 2008.

Chi et al., "Contemporary progresses on neutral, highly emissive Os(II) and Ru(II) complexes" Chemical Society Reviews, vol. 36, No. 9, Sep. 2007, pp. 1385-1532.

Chen et al., "New Series of Ruthenium(II) and Osmium(II) Complexes Showing Solid-State Phosphorescence in Far-Visible and Near-Infrared" Inorg. Chem. 2010, 49, 823-832.

Kirgan et al., "Photochemistry and Photophysics of Coordination Compounds: Rhenium" Top Curr Chem (2007) 281: 45-100.

Baldo et al., "Highly Efficient Phosphorescent Emission from Organic Electroluminescent Devices," Nature, vol. 395, 151-154, (1998).

Baldo et al., "Very high-efficiency green organic light-emitting devices based on electrophosphorescence," Appl. Phys. Lett., vol. 75, No. 3, 4-6 (1999).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Tung, Yung-Liang et al., "Organic Light-Emitting Diodes Based on Charge-Neutral $Ru^{II}$ PHosphorescent Emitters," Adv. Mater., 17(8):1059-1064 (2005).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Wong, Wai-Yeung, "Multifunctional Iridium Complexes Based on Carbazole Modules as Highly Efficient Electrophosphors," Angew. Chem. Int. Ed., 45:7800-7803 (2006).

Tang, C.W. and Vanslyke, S.A., "Organic Electroluminescent Diodes," App. Phys. Lett, 51(12):913-915 (1987).

Adachi, Chihaya et al., "Organic Electroluminescent Device Having a Hole Conductor as an Emitting Layer," Appl. Phys. Lett., 55(15):1489-1491 (1989).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

(56) References Cited

OTHER PUBLICATIONS

Gao, Zhigiang et al., "Bright-Blue Electroluminescence From a Silyl-Substituted ter-(phenylene-vinylene) derivative," *Appl. Phys. Lett.*, 74(6):865-867 (1999).

Lee, Chang-Lyoul et al., "Polymer Phosphorescent Light-Emitting Devices Doped with Tris(2-phenylpyridine) Iridium as a Triplet Emitter," *Appl. Phys. Lett.*, 77(15):2280-2282 (2000).

Hung, L.S. et al., "Anode Modification in Organic Light-Emitting Diodes by Low-Frequency Plasma Polymerization of $CHF_3$," *Appl. Phys. Lett.*, 78(5):673-675 (2001).

Ikai, Masamichi and Tokito, Shizuo, "Highly Efficient Phosphorescence From Organic Light-Emitting Devices with an Exciton-Block Layer," *Appl. Phys. Lett.*, 79(2):156-158 (2001).

Wang, Y. et al., "Highly Efficient Electroluminescent Materials Based on Fluorinated Organometallic Iridium Compounds," *Appl. Phys. Lett.*, 79(4):449-451 (2001).

Kwong, Raymond C. et al., "High Operational Stability of Electrophosphorescent Devices," *Appl. Phys. Lett.*, 81(1):162-164 (2002).

Holmes, R.J. et al., "Blue Organic Electrophosphorescence Using Exothermic Host-Guest Energy Transfer," *Appl. Phys. Lett.*, 82(15):2422-2424 (2003).

Sotoyama, Wataru et al., "Efficient Organic Light-Emitting Diodes with Phosphorescent Platinum Complexes Containing NCN-Coordinating Tridentate Ligand," *Appl. Phys. Lett.*, 86:153505-1-153505-3 (2005).

Okumoto, Kenji et al., "Green Fluorescent Organic Light-Emitting Device with External Quantum Efficiency of Nearly 10%," *Appl. Phys. Lett.*, 89:063504-1-063504-3 (2006).

Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1-123509-3 (2007).

Aonuma, Masaki et al., "Material Design of Hole Transport Materials Capable of Thick-Film Formation in Organic Light Emitting Diodes," *Appl. Phys. Lett.*, 90:183503-1-183503-3 (2007).

Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).

Adachi, Chihaya et al., "High-Efficiency Red Electrophosphorescence Devices," *Appl. Phys. Lett.*, 78(11):1622-1624 (2001).

Wong, Keith Man-Chung et al., A Novel Class of Phosphorescent Gold(III) Alkynyl-Based Organic Light-Emitting Devices with Tunable Colour, *Chem. Commun.*, 2906-2908 (2005).

Hamada, Yuji et al., "High Luminance in Organic Electroluminescent Devices with Bis(10-hydroxybenzo[h]quinolinato)beryllium as an Emitter," *Chem. Lett.*, 905-906 (1993).

Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).

Mi, Bao-Xiu et al., "Thermally Stable Hole-Transporting Material for Organic Light-Emitting Diode: an Isoindole Derivative," *Chem. Mater.*, 15(16):3148-3151 (2003).

Huang, Wel-Sheng et al., "Highly Phosphorescent Bis-Cyclometalated Iridium Complexes Containing Benzoimidazole-Based Ligands," *Chem. Mater.*, 16(12):2480-2488 (2004).

Niu, Yu-Hua et al., "Highly Efficient Electrophosphorescent Devices with Saturated Red Emission from a Neutral Osmium Complex," *Chem. Mater.*, 17(13):3532-3536 (2005).

Lo, Shih-Chun et al., "Blue Phosphorescence from Iridium(III) Complexes at Room Temperature," *Chem. Mater.*, 18(21):5119-5129 (2006).

Takizawa, Shin-ya et al., "Phosphorescent Iridium Complexes Based on 2-Phenylimidazo[1,2- α]pyridine Ligands: Tuning of Emission Color toward the Blue Region and Application to Polymer Light-Emitting Devices," *Inorg. Chem.*, 46(10):4308-4319 (2007).

Lamansky, Sergey et al., "Synthesis and Characterization of Phosphorescent Cyclometalated Iridium Complexes," *Inorg. Chem.*, 40(7):1704-1711 (2001).

Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).

Noda, Tetsuya and Shirota, Yasuhiko, "5,5'-Bis(dimesitylboryl)-2,2'-bithiophene and 5,5"-Bis(dimesitylboryl)-2,2:5',2"-terthiophene as a Novel Family of Electron-Transporting Amorphous Molecular Materials," *J. Am. Chem. Soc.*, 120 (37):9714-9715 (1998).

Sakamoto, Youichi et al., "Synthesis, Characterization, and Electron-Transport Property of Perfluorinated Phenylene Dendrimers," *J. Am. Chem. Soc.*, 122(8):1832-1833 (2000).

Adachi, Chihaya et al., "Nearly 100% Internal Phosphorescence Efficiency in an Organic Light Emitting Device," *J. Appl. Phys.*, 90(10):5048-5051 (2001).

Shirota, Yasuhiko et al., "Starburst Molecules Based on π-Electron Systems as Materials for Organic Electroluminescent Devices," *Journal of Luminescence*, 72-74:985-991 (1997).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).

Kido, Junji et al., 1,2,4-Triazole Derivative as an Electron Transport Layer in Organic Electroluminescent Devices, *Jpn. J. Appl. Phys.*, 32:L917-L920 (1993).

Van Slyke, S. A. et al., "Organic Electroluminescent Devices with Improved Stability," *Appl. Phys. Lett.*, 69(15 ):2160-2162 (1996).

Guo, Tzung-Fang et al., "Highly Efficient Electrophosphorescent Polymer Light-Emitting Devices," *Organic Electronics*, 1:15-20 (2000).

Palilis, Leonidas C., "High Efficiency Molecular Organic Light-Emitting Diodes Based on Silole Derivatives and Their Exciplexes," *Organic Electronics*, 4:113-121 (2003).

Ikeda, Hisao et al., "P-185: Low-Drive-Voltage OLEDs with a Buffer Layer Having Molybdenum Oxide," *SID Symposium Digest*, 37:923-926 (2006).

T. Östergård et al., "Langmuir-Blodgett Light-Emitting Diodes of Poly(3-Hexylthiophene): Electro-Optical Characteristics Related to Structure," *Synthetic Metals*, 87:171-177 (1997).

Hu, Nan-Xing et al., "Novel High $T_g$ Hole-Transport Molecules Based on Indolo[3,2- b]carbazoles for Organic Light-Emitting Devices," *Synthetic Metals*, 111-112:421-424 (2000).

Salbeck, J. et al., "Low Molecular Organic Glasses for Blue Electroluminescence," *Synthetic Metals*, 91:209-2'15 (1997).

\* cited by examiner

Formula I

RUTHENIUM CARBENE COMPLEXES FOR OLED MATERIAL

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to ruthenium carbene complexes. More specifically, it relates to bidentate nitrogen heterocyclic carbene complexes of ruthenium. These materials may be used in OLEDs to provide devices having improved performance.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine)iridium, denoted Ir(ppy)$_3$, which has the following structure:

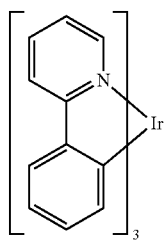

In this, and later figures herein, we depict the dative bond from nitrogen to metal (here, Tr) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Compounds comprising ruthenium (II) complexes having at least one carbene ligand bound to the ruthenium through a carbene bond and having the formula I are provided:

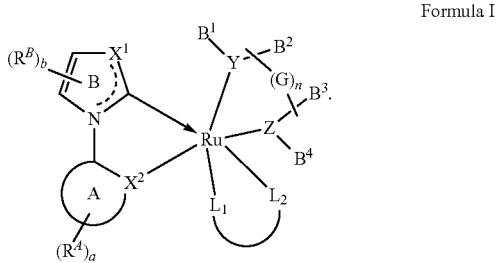

Formula I

The complex has an overall neutral charge. Ligand $L_1$-$L_2$ is a bidentate ligand bearing a single negative charge. The auxiliary ligand

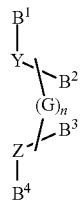

bears no net charge. A is an aromatic 5-membered or 6-membered carbocyclic or heterocyclic ring. $R^A$ may represent mono, di, tri, or tetra substitution, or no substitution. Each $R^A$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfonyl, phosphino, and combinations thereof. $R^A$ may also be optionally linked to ring A to form a fused ring or rings, which may be further substituted.

$X^1$ is a heteroatom that may be N—R', O, and S. $X^2$ may be carbon or nitrogen.

B is a 5-membered heterocyclic ring. $R^B$ may represent mono, di, tri, or tetra substitution, or no substitution. Each $R^B$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. $R^B$ may also be optionally linked to ring B to form a fused ring or rings, which may be further substituted.

Y and Z are independently selected from the group consisting of carbon, nitrogen, and phosphorus. Y is further substituted by $B^1$ and $B^2$, and Z is further substituted by $B^3$ and $B^4$. $B^1$, $B^2$, $B^3$, $B^4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfonyl, sulfonyl, phosphino, and combinations thereof.

$B^1$ and $B^2$ may also be optionally linked to form a 5- or 6-membered cyclic group having from 0 to 4 ring heteroatoms, and an 8- to 10-membered fused bicyclic group having from 0 to 4 ring heteroatoms. The 5- or 6-membered cyclic group having from 0 to 4 ring heteroatoms, and the 8- to 10-membered fused bicyclic group having from 0 to 4 ring heteroatoms may be optionally substituted with one or more substituents independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

$B^3$ and $B^4$ may also be optionally linked to form a 5- or 6-membered cyclic group having from 0 to 4 ring heteroatoms, and an 8- to 10-membered fused bicyclic group having from 0 to 4 ring heteroatoms. The 5- or 6-membered cyclic group having from 0 to 4 ring heteroatoms, and the 8- to 10-membered fused bicyclic group having from 0 to 4 ring heteroatoms may be optionally substituted with one or more substituents independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

G is selected from the group consisting of an alkyl and alkenyl having from 1 to 5 carbon atoms. A first end of G is bonded is to Y or $B^2$, and a second end of G is bonded to Z or $B^3$. When n is 0, G is absent, and when n is 1, G is present.

R' is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the compound has the formula II:

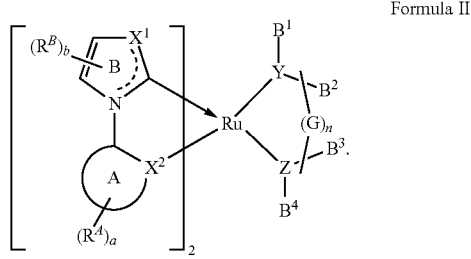

Formula II

In one aspect, the compound has the formula III:

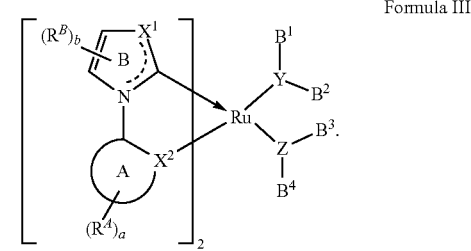

Formula III

In one aspect, the compound has the formula IV:

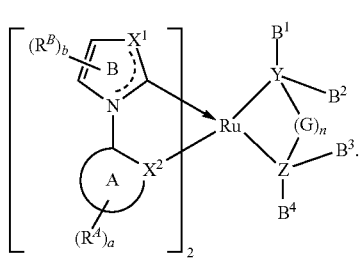

Formula IV

In one aspect, the compound has the formula V:

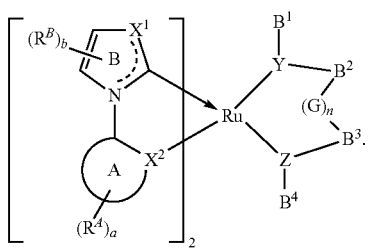

Formula V

In one aspect, the compound has the formula VI:

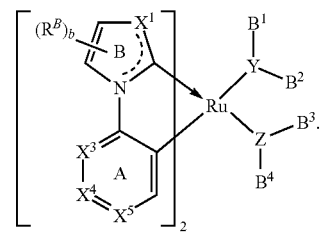

Formula VI $X^3$ is selected from the group C—$R^1$ and N, $X^4$ is selected from the group C—$R^2$ and N, and $X^5$ is selected from the group C—$R^3$ and N. $R^1$, $R^2$, and $R^3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the compound has the formula VII:

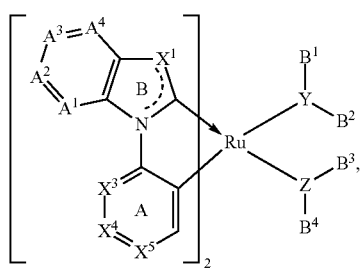

Formula VII where $A^1$, $A^2$, $A^3$, and $A^4$ are independently selected from the group consisting of C—R' and N.

In one aspect, the compound has the formula VIII:

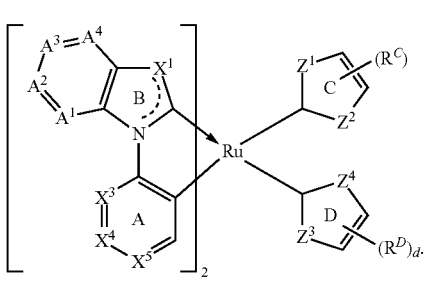

Formula VIII

Rings C and D are preferably 5-membered ring heterocycles. $R^C$ and $R^D$ each independently represent mono-, di-, tri-, or tetra-substitution. Each $R^C$ and $R^D$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. $Z^1$, $Z^2$, $Z^3$, and $Z^4$ are independently selected from N—R', S, and O.

In one aspect, the compound has the formula IX:

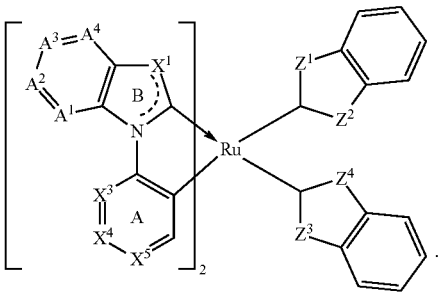

Formula IX

In one aspect, the compound has the formula X:

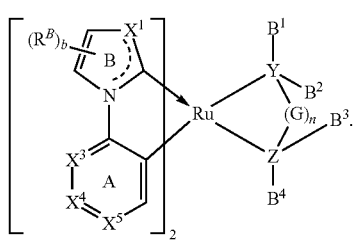

Formula X

In one aspect, the compound has the formula XI:

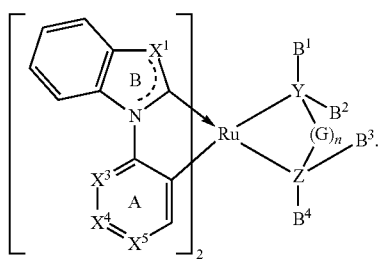

Formula XI

In one aspect, the compound has the formula XII:

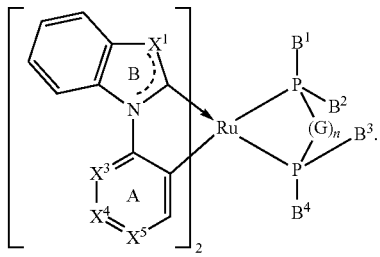

Formula XII

In one aspect, the compound has the formula XIII:

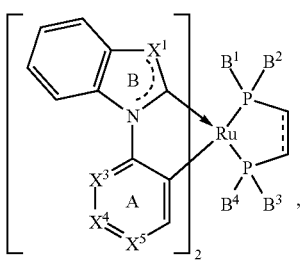

Formula XIII where the dashed line on the phosphine ligand represents an optional bond.

In one aspect, the compound has the formula XIV:

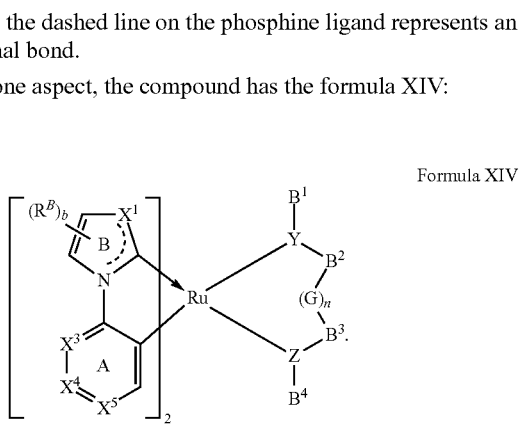

Formula XIV

In one aspect, the compound has the formula XV:

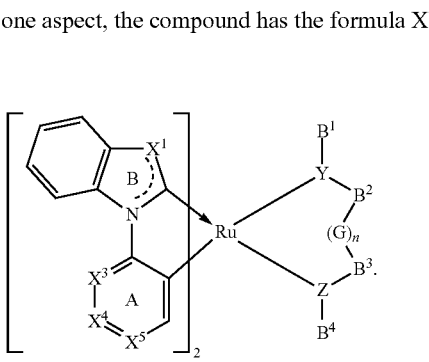

Formula XV

In one aspect, the compound has the formula XVI:

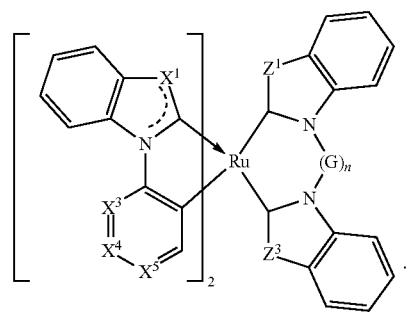

Formula XVI

In one aspect, the compound has the formula XVII:

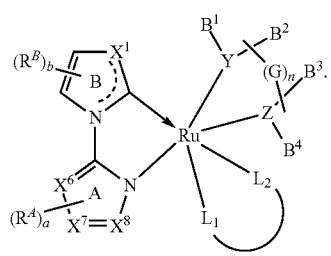

Formula XVII

In one aspect, ring A is 5-membered heterocycle bound to the ruthenium through nitrogen, $X^6$ is selected from the group C—R' and N, $X^7$ is selected from the group C—$R^2$ and N, and $X^8$ is selected from the group C—$R^3$ and N.

In one aspect, the compound has the formula XVIII:

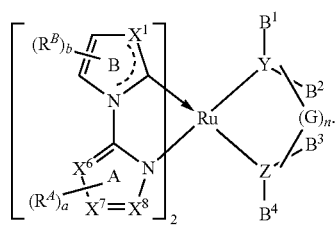

Formula XVIII

In one aspect, the compound has the formula XIX:

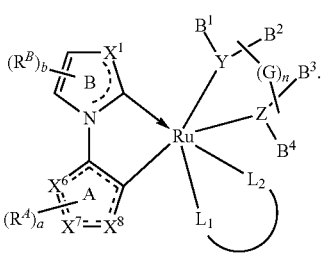

Formula XIX

In one aspect, ring A is a 5-membered heterocycle bound to the ruthenium through carbon, $X^6$ is selected from the group C—$R^1$, N, N—R', S, and O, $X^7$ is selected from the group C—$R^2$, N, N—R', S, and O, $X^8$ is selected from the group C—$R^3$, N, N—$R^1$, S, and O and the dashed line on ring A represents optional bonds. In one aspect, at least one of $X^6$, $X^7$, and $X^8$ is a heteroatom or substituted heteroatom.

In one aspect, the compound has the formula XX:

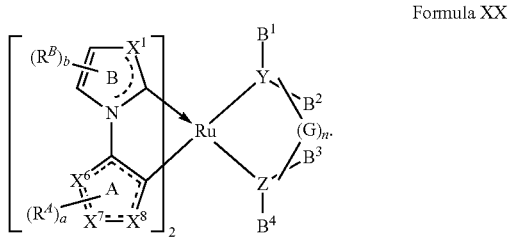

Formula XX

Specific non-limiting example compounds are provided. In one aspect, the compounds are selected from the group consisting of Compound 1-Compound 34.

Additionally, a first device comprising an organic light emitting device is provided. The organic light emitting device further comprises an anode, a cathode, and an organic layer disposed between the anode and the cathode. The organic layer comprises a compound of formula I.

In one aspect, the organic layer is an emissive layer and the compound is an emissive dopant. In one aspect, the organic layer further comprises a host.

In one aspect, the first device is a consumer product. In one aspect, the first device is an organic light emitting device.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
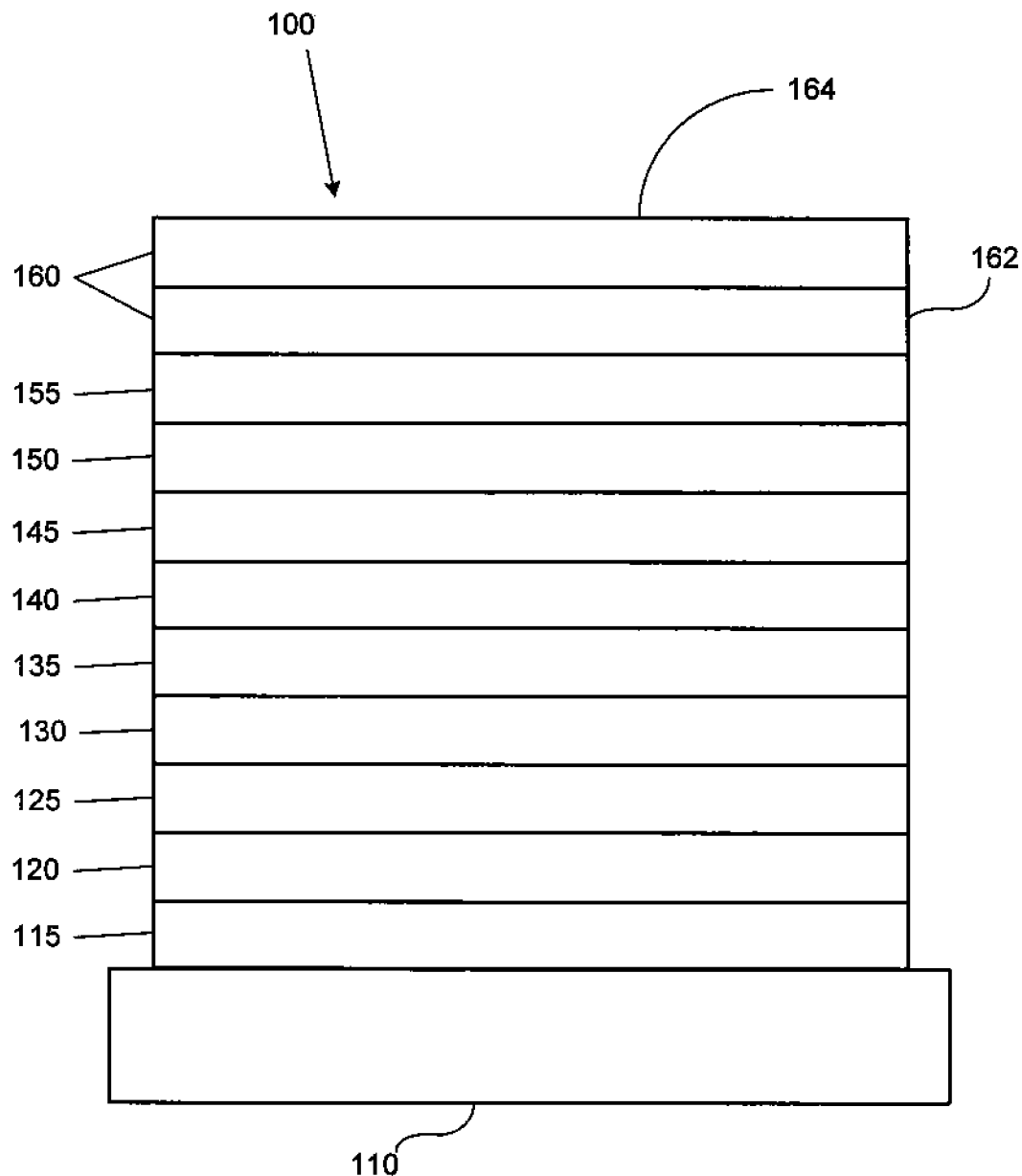
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
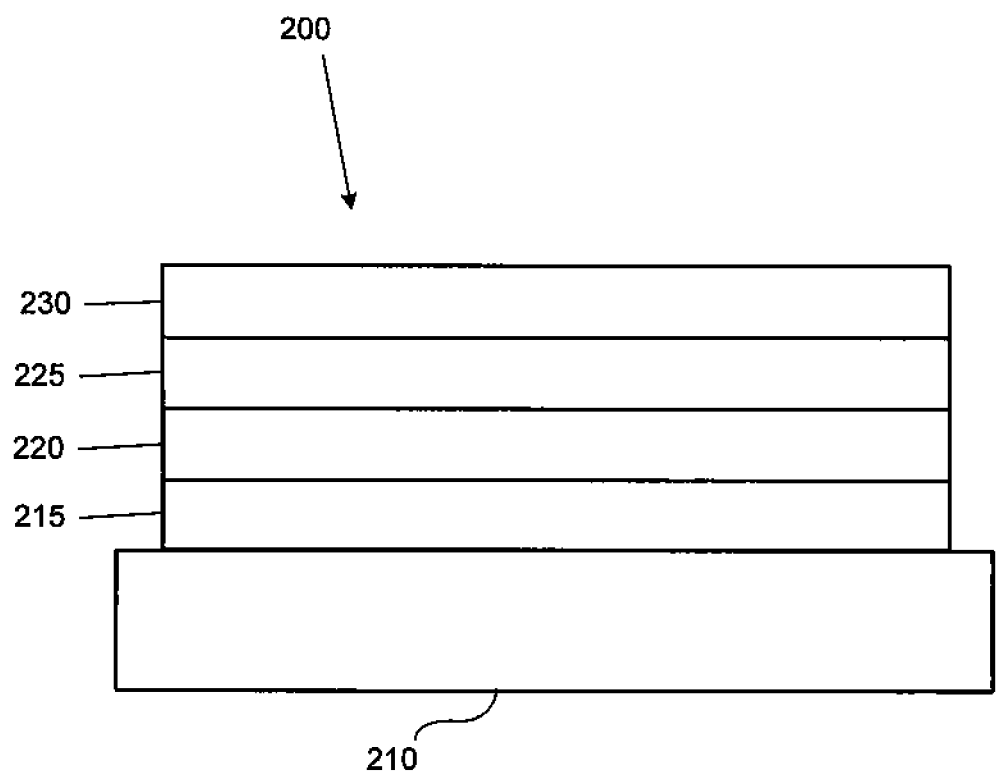
FIG. 2 shows an inverted organic light emitting device that does not have a separate electron transport layer.
Figure 3:
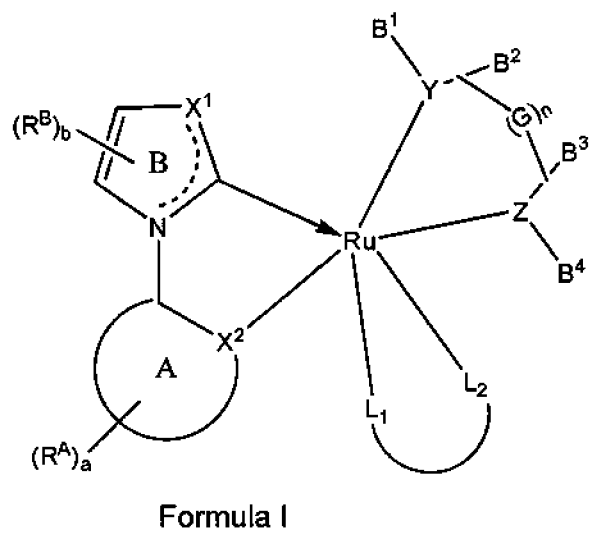
FIG. 3 shows a compound of formula I.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used.

Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Ruthenium complexes are generally weakly emissive due to the smaller ligand field strength found in complexes of second row transition metals. The ruthenium carbene complexes described herein overcome the weak emissivity of previously known second row transition metal complexes. Without limiting the claims to any theory of why the compounds are superior, the use of carbenes, which are strong field ligands, increases the energy gap of the metal-centered d-d transition, so that the radiationless deactivation associated with the metal-metal and metal-ligand bond strengthening can be significantly suppressed. The resulting ruthenium carbene complexes are more emissive (Scheme 1). The neutral ruthenium carbene complexes with at least one bidentate carbene ligand described herein are believed to be novel. These ruthenium carbene complexes can be used as phosphorescent dopants and HIL material(s) in OLED devices.

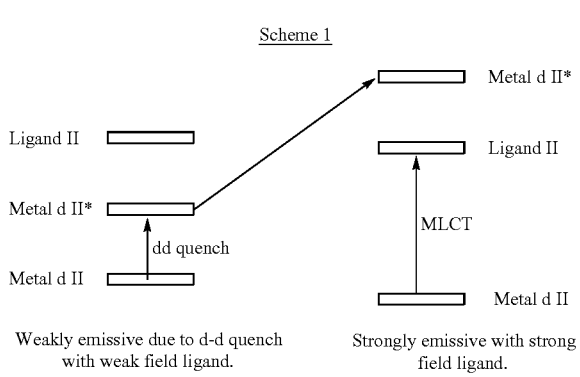

Scheme 1

Weakly emissive due to d-d quench with weak field ligand.

Strongly emissive with strong field ligand.

Compounds comprising ruthenium (II) complexes having at least one carbene ligand bound to the ruthenium through a carbene bond are provided, having the formula I:

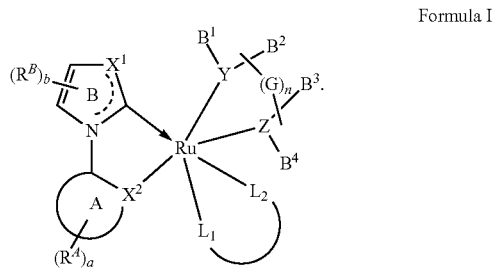

Formula I

The complex has an overall neutral charge.

$L_1-L_2$ is a bidentate ligand bearing a single negative charge. In one embodiment, $L_1-L_2$ is selected from the group consisting of:

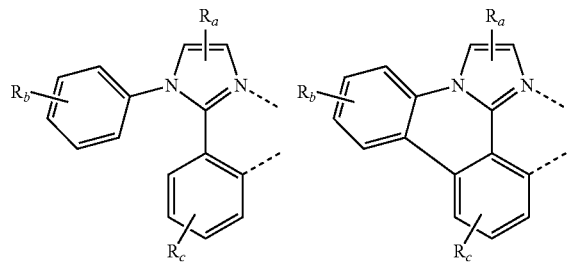

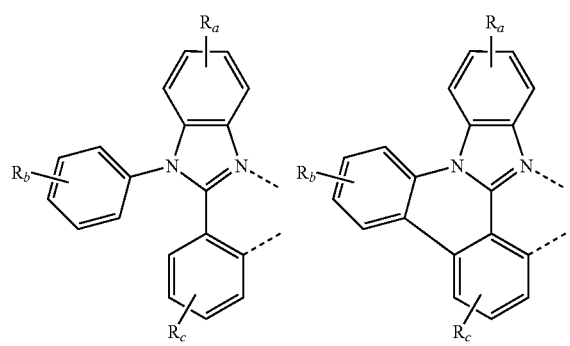

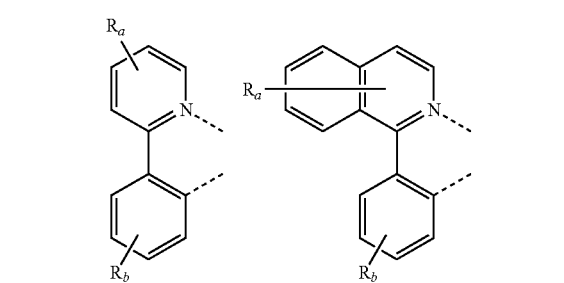

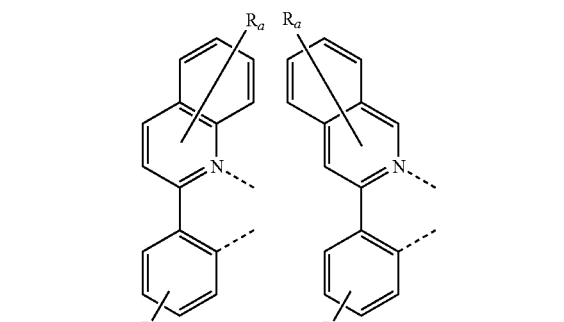

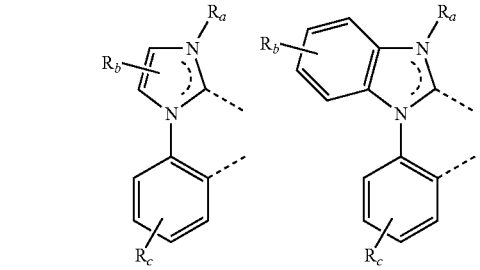

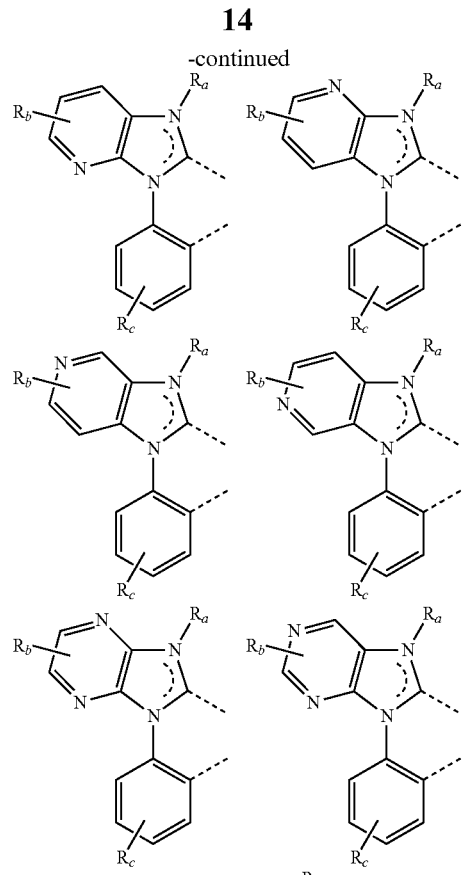

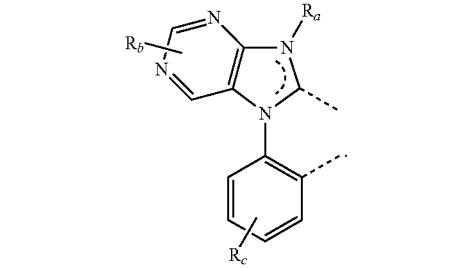

$R_a$, $R_b$, and $R_c$ may represent mono, di, tri or tetra substitutions. $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_a$, $R_b$, and $R_c$ are optionally joined to form a fused ring.

A is an aromatic 5-membered or 6-membered carbocyclic or heterocyclic ring. $R^A$ may represent mono, di, tri, or tetra substitution, or no substitution. Each $R^A$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof $R^A$ may also be optionally linked to ring A to form a fused ring or rings, which may be further substituted.

$X^1$ is a heteroatom that may be N—R', O, and S. $X^2$ may be carbon or nitrogen.

B is a 5-membered heterocyclic ring. $R^B$ may represent mono, di, tri, or tetra substitution, or no substitution. Each $R^B$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. $R^B$ may also be optionally linked to ring B to form a fused ring or rings, which may be further substituted.

The auxiliary ligand

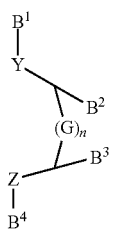

bears no net charge.

Y and Z are independently selected from the group consisting of carbon, nitrogen, and phosphorus. Y is further substituted by $B^1$ and $B^2$, and Z is further substituted by $B^3$ and $B^4$. $B^1$, $B^2$, $B^3$, $B^4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

$B^1$ and $B^2$ may also be optionally linked to form a 5- or 6-membered cyclic group having from 0 to 4 ring heteroatoms, and an 8- to 10-membered fused bicyclic group having from 0 to 4 ring heteroatoms. The 5- or 6-membered cyclic group having from 0 to 4 ring heteroatoms, and the 8- to 10-membered fused bicyclic group having from 0 to 4 ring heteroatoms may be optionally substituted with one or more substituents independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

$B^3$ and $B^4$ may also be optionally linked to form a 5- or 6-membered cyclic group having from 0 to 4 ring heteroatoms, and an 8- to 10-membered fused bicyclic group having from 0 to 4 ring heteroatoms. The 5- or 6-membered cyclic group having from 0 to 4 ring heteroatoms, and the 8- to 10-membered fused bicyclic group having from 0 to 4 ring heteroatoms may be optionally substituted with one or more substituents independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

G is selected from the group consisting of alkyl and alkenyl having from 1 to 5 carbon atoms. A first end of G is bonded is to Y or $B^2$, and a second end of G is bonded to Z or $B^3$. When n is 0, G is absent, and when n is 1, G is present.

When G is absent, an auxiliary ligand comprises two monodentate neutral ligands. In one embodiment, G is absent and the auxiliary ligand comprises two monodentate carbenes. In one embodiment, G is present and the auxiliary ligand comprises a phosphine. In one embodiment, G is present and the auxiliary ligand comprises a bidentate carbene coordinated to the ruthenium through two ruthenium-carbene bonds.

R' is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, $X^3$ is selected from the group $C—R^1$ and N, $X^4$ is selected from the group $C—R^2$ and N, and $X^5$ is selected from the group $C—R^3$ and N. $R^1$, $R^2$, and $R^3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, rings C and D are preferably 5-membered ring heterocycles. $R^C$ and $R^D$ each independently represent mono-, di-, tri-, or tetra-substitution. Each $R^C$ and $R^D$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. $Z^1$, $Z^2$, $Z^3$, and $Z^4$ are independently selected from N—R', S, and O.

In one embodiment, ring A is 5-membered heterocycle bound to the ruthenium through nitrogen, $X^6$ is selected from the group $C—R^1$ and N, $X^7$ is selected from the group $C—R^2$ and N, and $X^8$ is selected from the group $C—R^3$ and N.

In one embodiment, ring A is a 5-membered heterocycle bound to the ruthenium through carbon, $X^6$ is selected from the group $C—R^1$, N, N—R', S, and O, $X^7$ is selected from the group $C—R^2$, N, N—R', S, and O, $X^8$ is selected from the group $C—R^3$, N, N—R', S, and O and the dashed line on ring A represents optional bonds. In one embodiment, at least one of $X^6$, $X^7$, and $X^8$ is a heteroatom or substituted heteroatom.

In one embodiment, $L_1$-$L_2$ can have the same structure as at least one other carbene ligand coordinated to the ruthenium. In one embodiment, the compound has the structure of formula II. By varying the number of carbene ligands coordinated to the ruthenium, the emissivity of the ruthenium complex can be tuned.

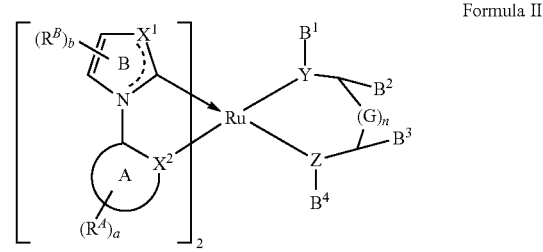

Formula II

In one embodiment, the compound has the formula III.

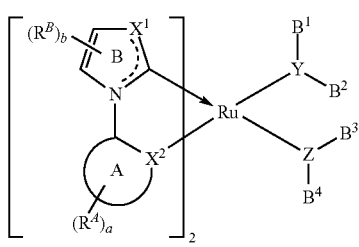

Formula III

The compound of formula III has two neutral monodentate ligands coordinated to the ruthenium, $B^1$—Y—$B^2$ and $B^3$—Z—$B^4$, which may be the same or different.

In one embodiment ring A is an aromatic 6-membered carbocycle or heterocycle in a compound of formula VI.

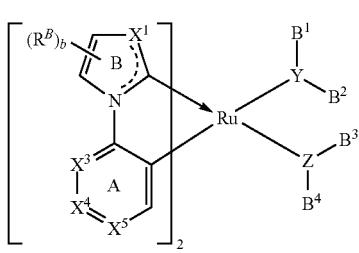

Formula VI

Metallation of the aryl C—H bond gives rise to a carbon bearing a single negative charge, which is coordinated to the ruthenium center.

In a preferred embodiment, a 6-membered aromatic ring is fused to ring B to give a compound of formula VII. $A^1$, $A^2$, $A^3$, and $A^4$ are independently selected from the group consisting of C—R' and N.

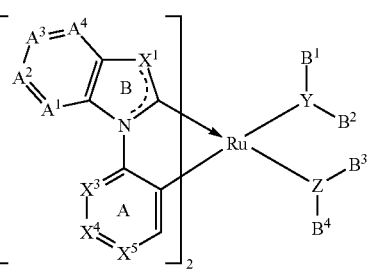

Formula VII

Although any of the substitutions disclosed herein may be present on ring B, benzimidazole ($X^1$=N—R'), benzoxazole ($X^1$=O), and benzothiazole ($X^1$=S) derivatives as well as the corresponding aza derivatives (e.g. one or more of $A^1$, $A^2$, $A^3$, and $A^4$ is N) are preferred due to the relatively good availability of starting materials and/or the availability of a variety of chemistries for their synthesis.

In one embodiment, the auxiliary ligand comprises two monodentate carbene ligands in a compound of formula VIII.

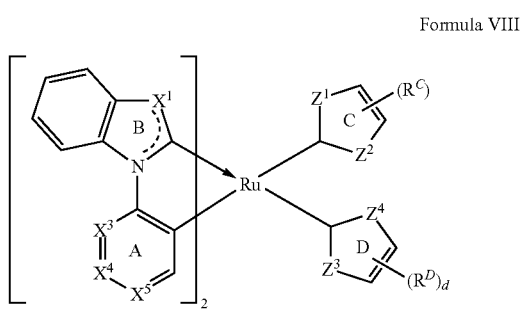

Formula VIII

In one embodiment, the auxiliary ligands can be benzo derivatives of imidazoles, oxazoles, or thiazoles, as in a compound of formula IX, although other functionality (e.g. $Z^1$=$Z^2$=O) is also possible.

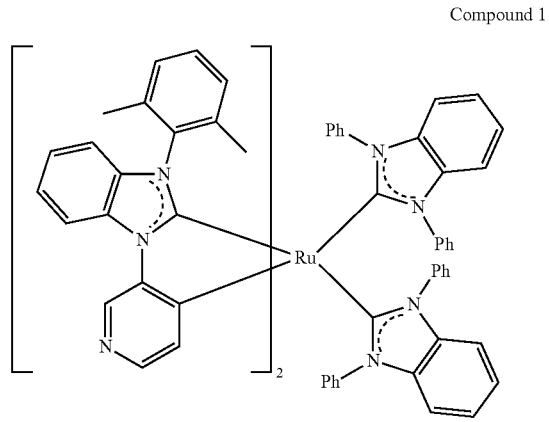

Formula IX

In one embodiment, the compounds are selected from a group consisting of Compound 1-Compound 13.

Compound 1

-continued
Compound 2
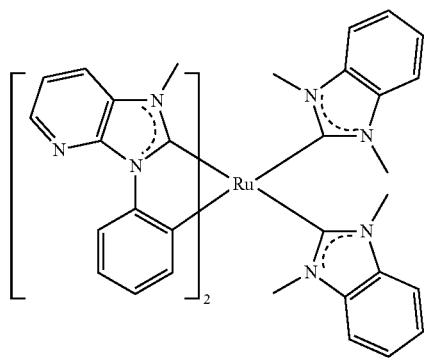
Compound 3
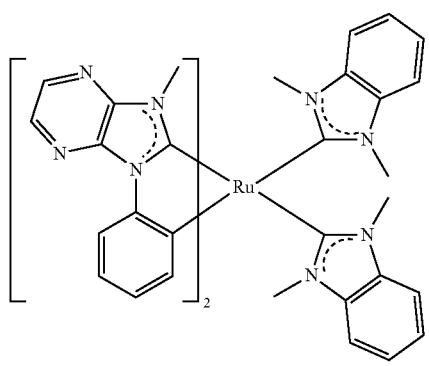
Compound 4
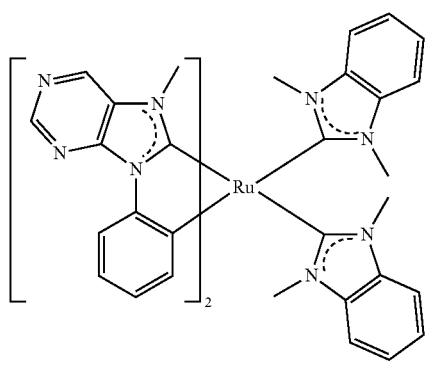
Compound 5
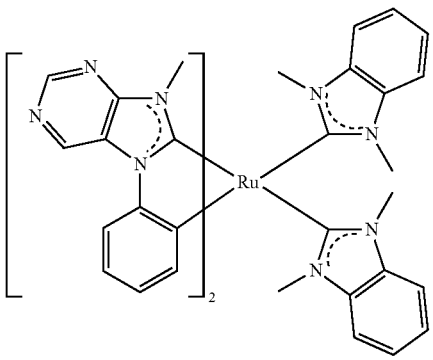
-continued
Compound 6
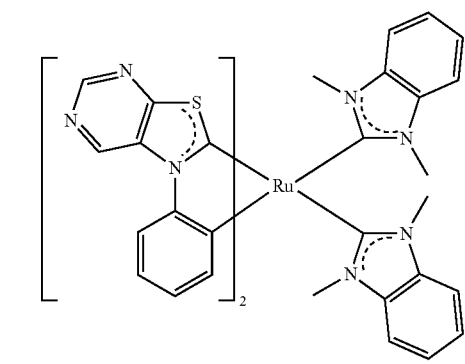
Compound 7
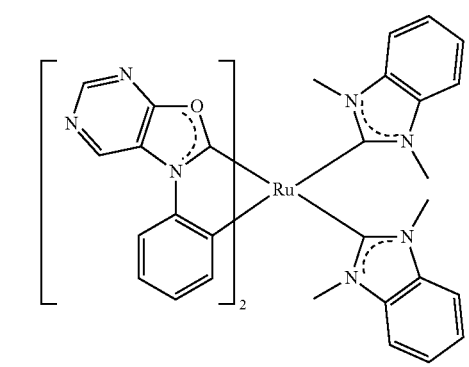
Compound 8
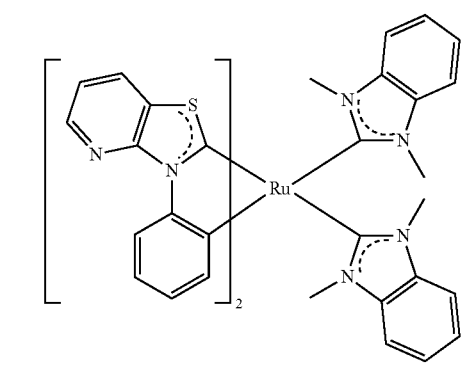
Compound 9
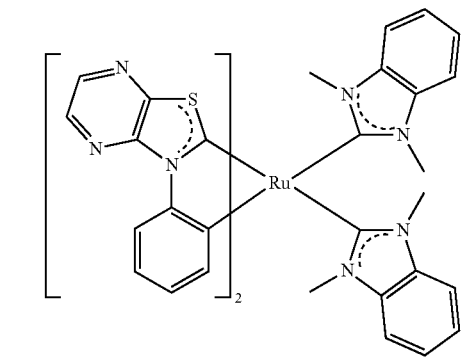

Compound 10

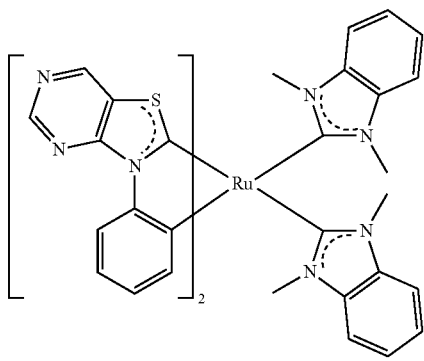

Compound 11

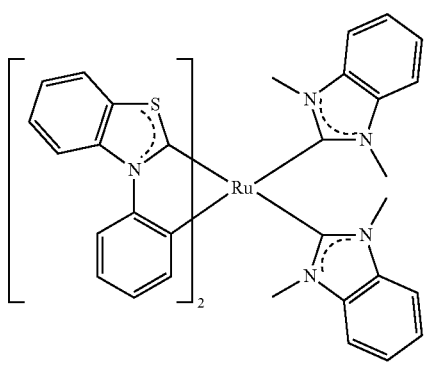

Compound 12

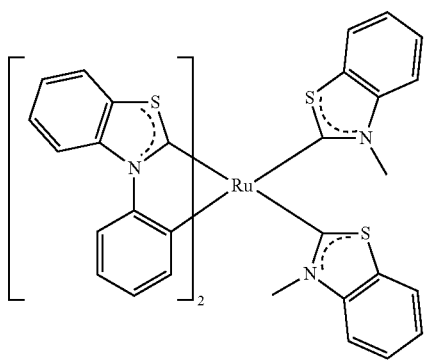

Compound 13

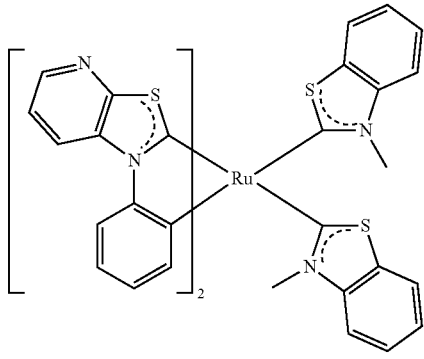

In one embodiment, a compound can have the formula IV.

Formula IV

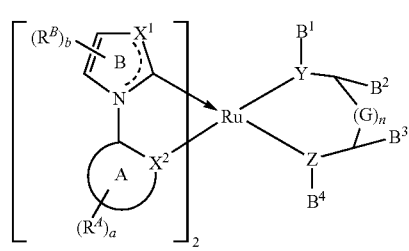

In this embodiment, n=1 and G is present, and $B^1$—Y—$B^2$ and $B^3$—Z—$B^4$ are linked together through atoms Y and Z.

In one embodiment, a compound may have the formula X or XI.

Formula X

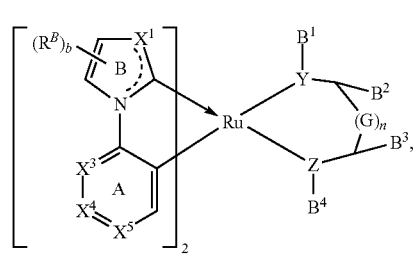

Formula XI

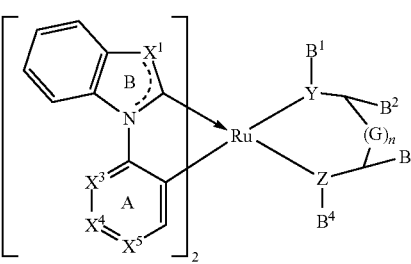

In a preferred embodiment, the auxiliary ligand is a bidentate phosphine in a compound of formula XII. In a more preferred embodiment, the compound has the formula XIII.

Formula XII

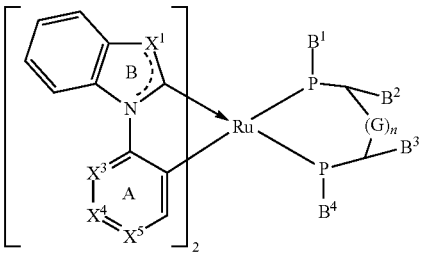

Formula XIII

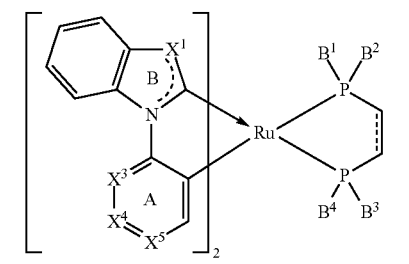

As discussed above, G can be from 1 to 5 carbons long, and can be alkyl or alkenyl. Bidentate phosphines having carbon chain lengths with more than five carbon atoms tend to be poor ligands due to the large number of possible conformers in such compounds, resulting in high entropic barriers to coordinate with a metal center. Preferably, G is 3 carbons in length, and most preferably 2 carbons in length. These carbon chain lengths allows the auxiliary phosphine ligand to have a more favorable bite angle for coordination with the ruthenium center. The dashed line on the phoshphine ligand in the compound of formula XIII represents an optional bond.

In one embodiment, the compound is selected from the group consisting of Compound 14-Compound 18.

Compound 14

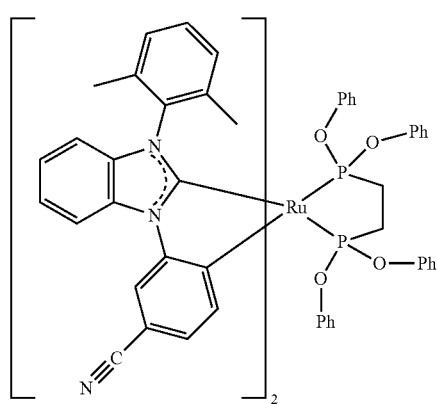

Compound 15

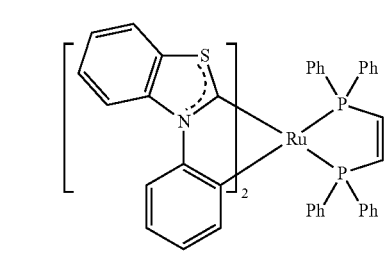

Compound 16

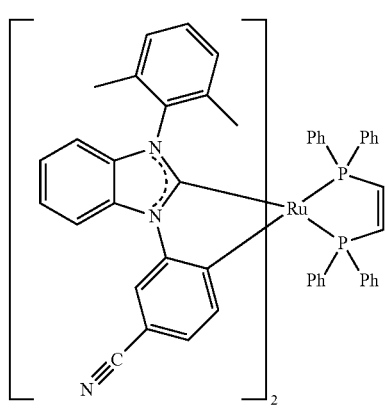

Compound 17

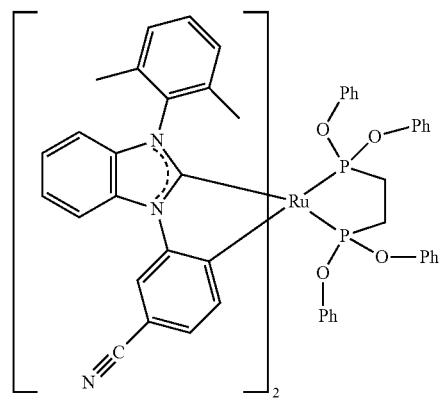

Compound 18

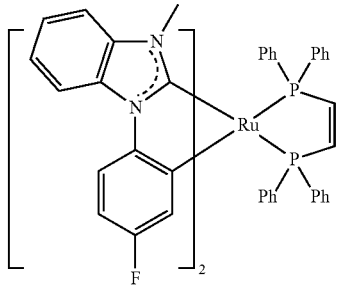

In one embodiment, a compound can have the formula V.

Formula V

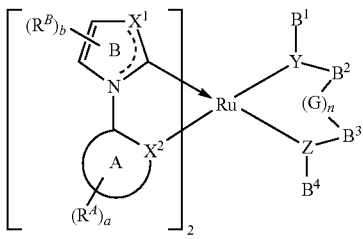

In this embodiment, n=1 and G is present. $B^1$—Y—$B^2$ and $B^3$—Z—$B^4$ are linked together through atoms present in groups $B^2$ and $B^3$.

In one embodiment, a compound can have the formula XIV. In one embodiment the compound can have the formula XV.

Formula XIV

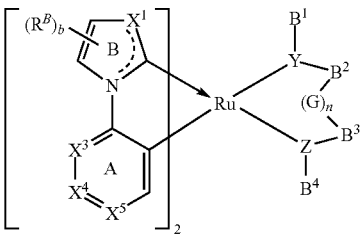

Formula XV

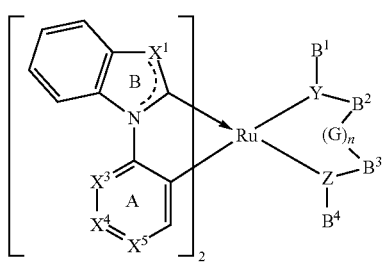

In a preferred embodiment, a compound has the formula XVI.

Formula XVI

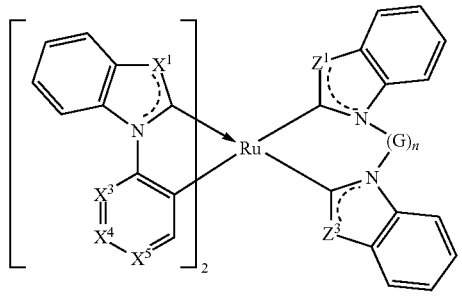

In this embodiment, the auxiliary ligand is a bidentate NHC (N-heterocyclic carbene) connected through a pair of nitrogen atoms. As discussed above, carbenes formed from benzimidazoles, benzoxazoles, and benzothiazoles (and their derivatives) are preferred. In the compound of formula XVI, G is a methylene group (i.e. one carbon chain), which allows the auxiliary bidentate carbene ligand to have a more favorable bite angle for coordination with the ruthenium center.

In one embodiment, the compound is selected from the group consisting of Compound 19-Compound 23.

Compound 19

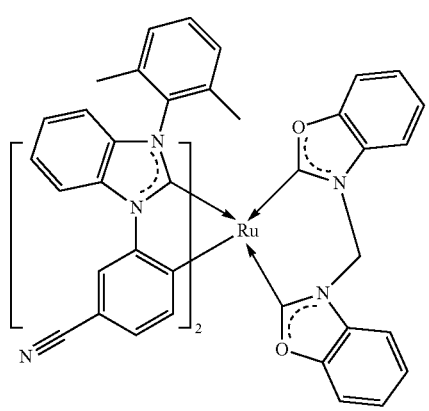

Compound 20

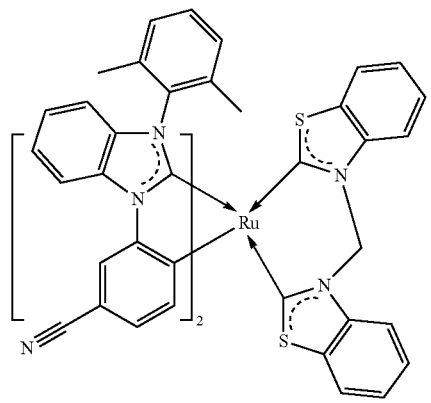

Compound 21

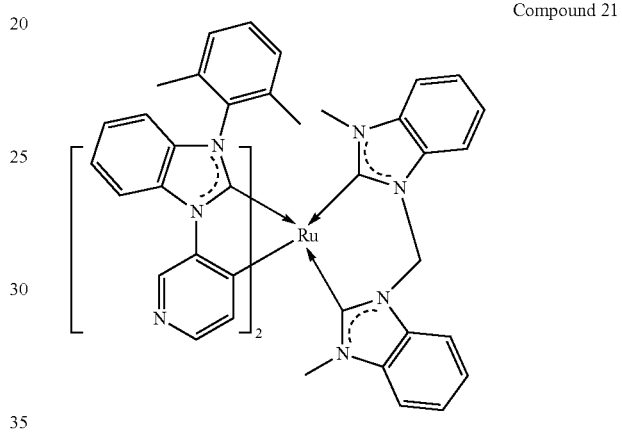

Compound 22

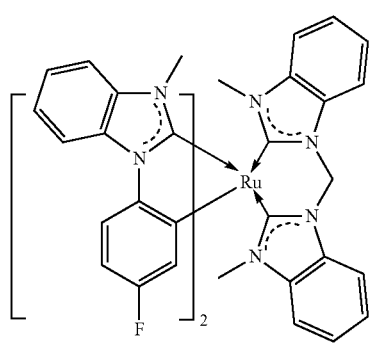

Compound 23

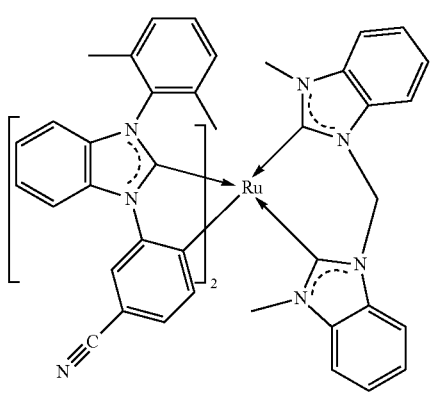

In one embodiment, the compound has the formula XVII:

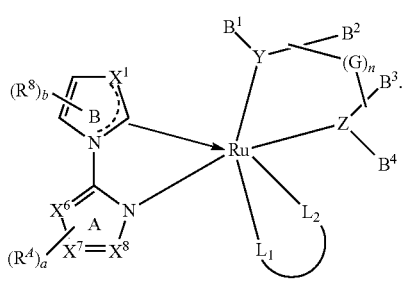

Formula XVII

In this embodiment, the single negative charge on the at least one carbene ligand is centered on the pyrrole nitrogen of ring A.

In one embodiment, the compound has the formula XIX:

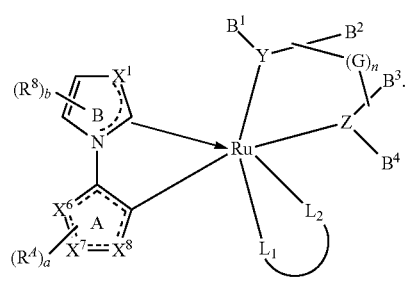

Formula XIX

In this embodiment, the single negative charge is on a carbon atom present in ring A as a result of metallation of an aromatic C—H bond. At least one of $X^6$, $X^7$, and $X^8$ is a heteroatom or substituted heteroatom selected from the group consisting of N—R', N, O, and S.

In one embodiment, ligand $L_1$-$L_2$ has the same structure as at least one carbene ligand coordinated to the ruthenium. In one embodiment, the compound has the formula XVIII. In one embodiment, the compound has the formula XX.

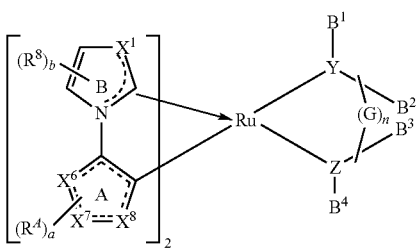

Formula XX

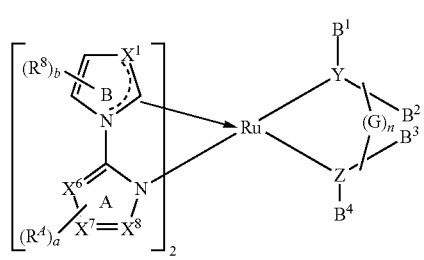

Formual XVIII

In one embodiment, the compound is selected from the group consisting of Compound 24-Compound 34.

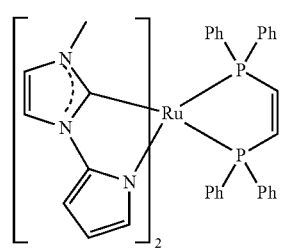

Compound 24

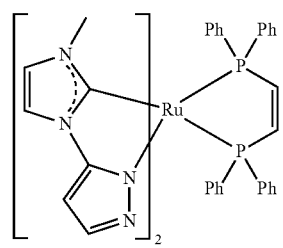

Compound 25

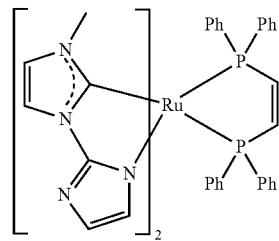

Compound 26

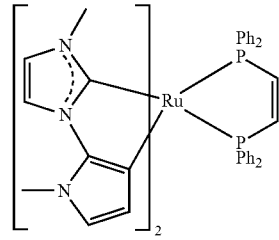

Compound 27

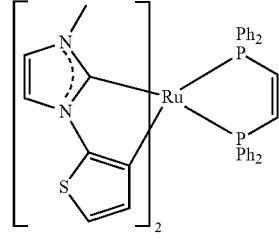

Compound 28

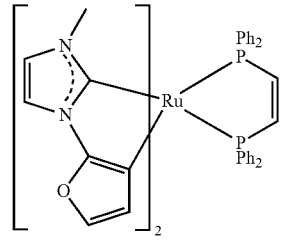

Compound 29

-continued

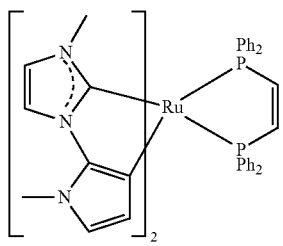
Compound 30

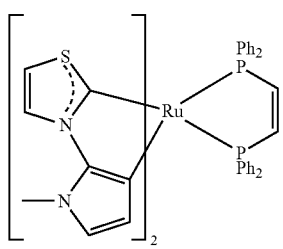
Compound 31

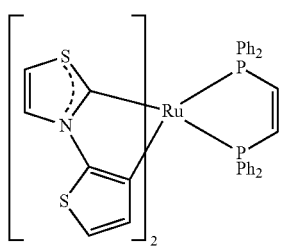
Compound 32

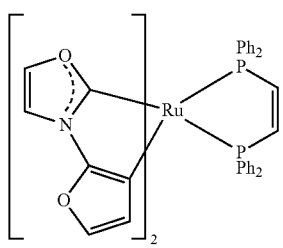
Compound 33

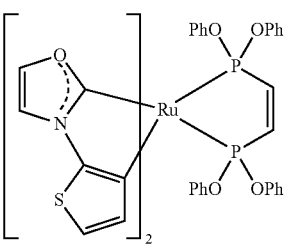
Compound 34

An organic light emitting device is also provided. The device may include an anode, a cathode, and an organic emissive layer disposed between the anode and the cathode. The organic emissive layer may includes a host and a phosphorescent dopant. In one embodiment, the organic emissive layer comprises a compound of formula I. In one embodiment, the organic layer is an emissibe layer, and the compound of formula I is an emissive dopant. In one embodiment, the organic layer comprises a host. In one embodiment, the first device is a consumer product. In one embodiment, the first device is an organic light emitting device.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in some embodiments of the present invention is not particularly limited, and any compound may be used as long as the compound is typically used as a hole injecting/transporting material. Examples of the material may include, but are not limited to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and slime derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL may include, but are not limited to, the following general structures:

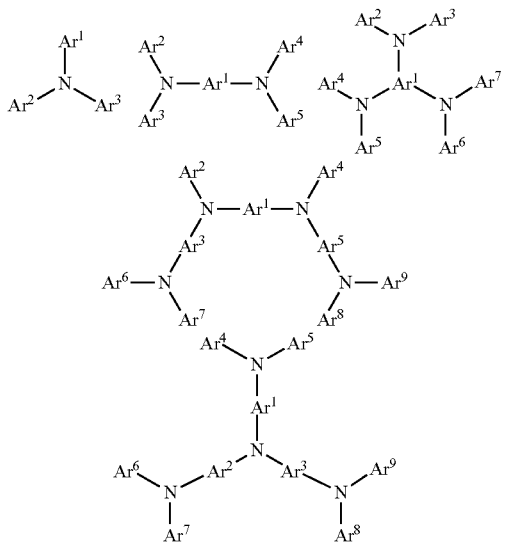

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, fiuran, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfonyl, sulfonyl, phosphino, and combinations thereof.

In one aspect, $Ar^1$ to $Ar^9$ is independently selected from the group consisting of:

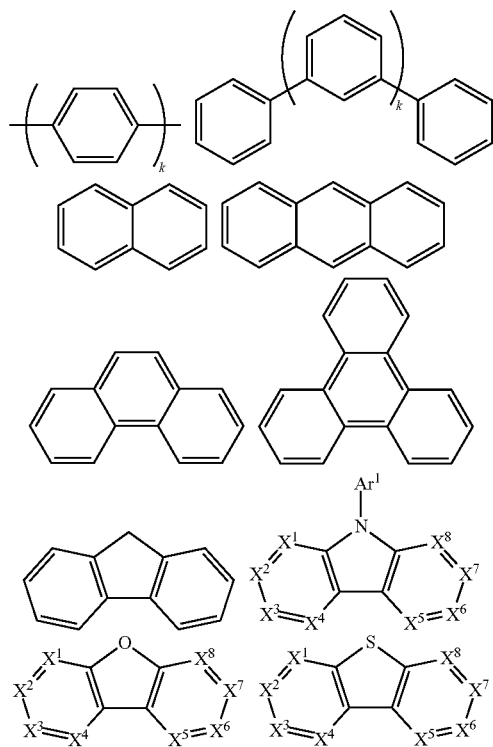

k is an integer from 1 to 20; $X^1$ to $X^8$ is CH or N; $Ar^1$ has the same group defined above.

Examples of metal complexes that may used in HIL or HTL include, but are not limited to, the following general formula:

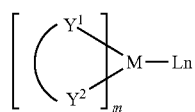

M is a metal having an atomic weight greater than 40; $(Y^1—Y^2)$ is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, $(Y^1—Y^2)$ is a 2-phenylpyridine derivative.
In one aspect, $(Y^1—Y^2)$ is a carbene ligand.
In one aspect, M is selected from Ir, Pt, Os, and Zn.
In a further aspect, the metal complex has a smallest oxidation potential in solution vs. Fc+/Fc couple less than about 0.6 V.

Host:

The light emitting layer of the organic EL device in some embodiments of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant.

Examples of metal complexes used as host materials are preferred to have the following general formula:

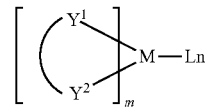

M is a metal; $(Y^3—Y^4)$ is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

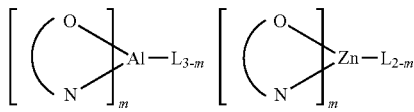

(O—N) is a bidentate ligand, having metal coordinated to atoms O and N.

In one aspect, M is selected from Ir and Pt.
In a further aspect, $(Y^3—Y^4)$ is a carbene ligand.
Examples of organic compounds used as host materials include materials selected from the group consisting of: aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the host compound contains at least one of the following groups in the molecule:

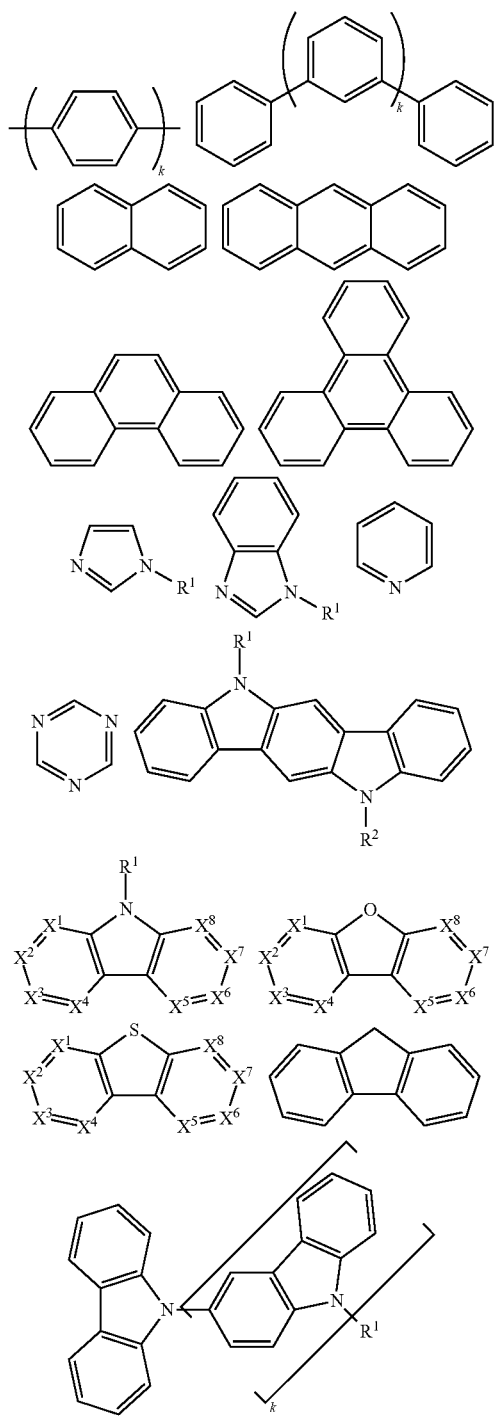

-continued

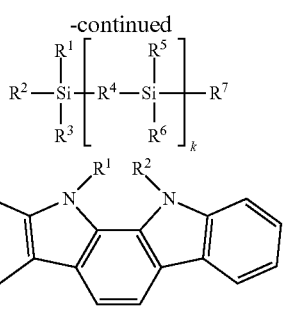

$R^1$ to $R^7$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfonyl, sulfonyl, phosphino, and combinations thereof, when it is aryl or heteroaryl, it has the similar definition as Ar's mentioned above.

k is an integer from 0 to 20.

$X^1$ to $X^8$ is selected from CH or N.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, the compound used in the HBL contains the same molecule used as host described above.

In one aspect, the compound used in the HBL contains at least one of the following groups in the molecule:

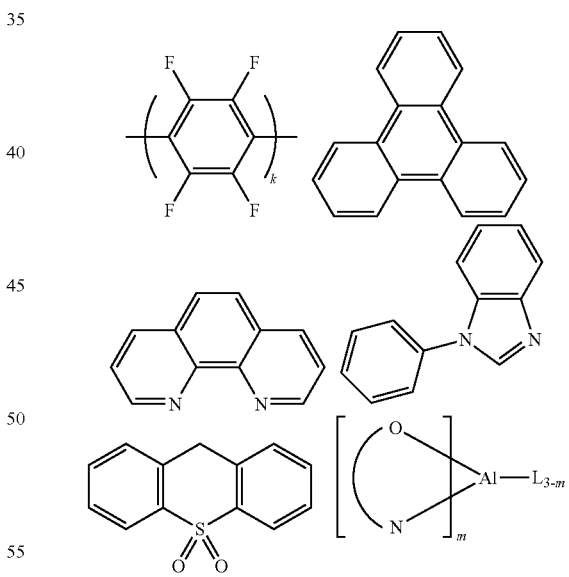

k is an integer from 0 to 20; L is an ancillary ligand, m is an integer from 1 to 3.

ETL:

The electron transport layer (ETL) may include a material capable of transporting electrons. The electron transport layer may be intrinsic (undoped) or doped. Doping may be used to enhance conductivity. Examples of the ETL material are not particularly limited, and any metal complexes or organic compounds may be used as long as they are typically used to transport electrons.

In one aspect, the compound used in the ETL contains at least one of the following groups in the molecule:

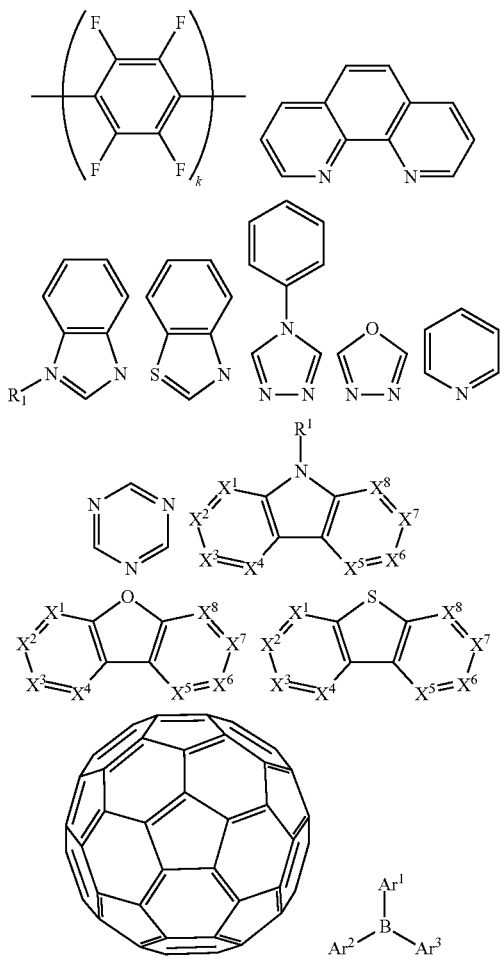

$R^1$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above.

k is an integer from 0 to 20.

$X^1$ to $X^8$ is selected from CH or N.

In one aspect, the metal complexes used in the ETL may contain, but are not limit to, the following general formula:

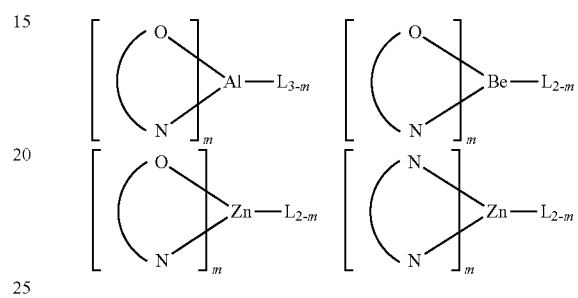

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of OLED device, the hydrogen atoms can be partially or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
|---|---|---|
| Hole injection materials | | |
| Phthalocyanine and porphryin compounds | 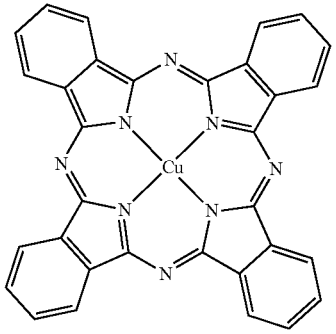 | Appl. Phys. Lett. 69, 2160 (1996) |

TABLE 1-continued
| MATERIAL | EXAMPLES OF MATERIAL | PUBLICATIONS |
|---|---|---|
| Starburst triarylamines | 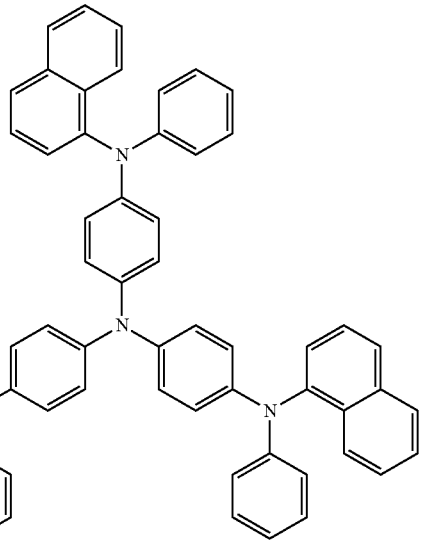 | J. Lumin. 72-74, 985 (1997) |
| $CF_x$ Fluorohydrocarbon polymer | $-\!\!+\!CH_xF_y\!+\!\!-_n$ | Appl. Phys. Lett. 78, 673 (2001) |
| Conducting polymers (e.g., PEDOT:PSS, polyaniline, polypthiophene) | 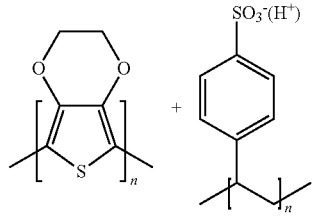 | Synth. Met. 87, 171 (1997) WO2007002683 |
| Phosphonic acid and sliane SAMs | 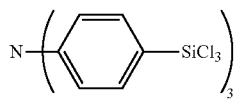 | US20030162053 |
| Triarylamine or polythiophene polymers with conductivity dopants | 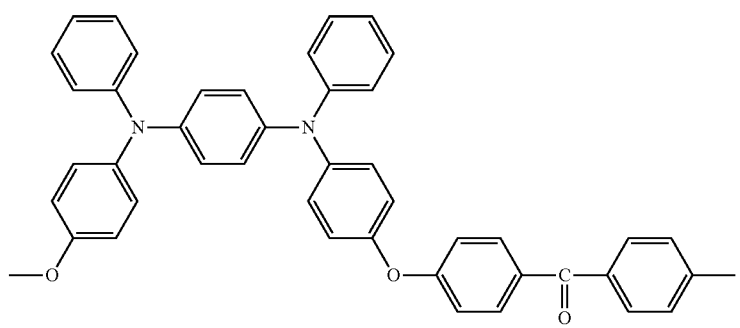 and | EA01725079A1 |

TABLE 1-continued
| MATERIAL | EXAMPLES OF MATERIAL | PUBLICATIONS |
|---|---|---|
| | 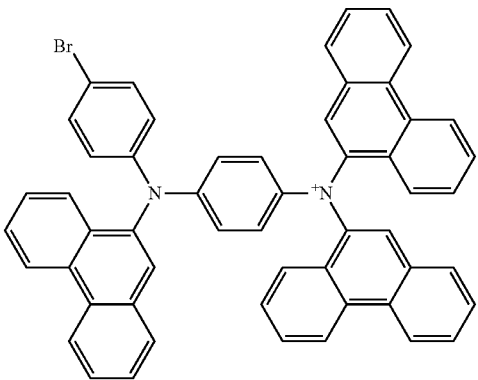 [SMILES: Brc1ccc(N(c2ccc([NH+](c3cc4ccccc4c4ccccc34)c3cc4ccccc4c4ccccc34)cc2)c2cc3ccccc3c3ccccc23)cc1] | |
| | 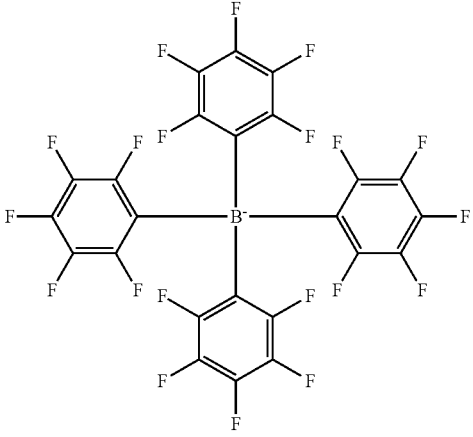 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | |
| Arylamines complexed with metal oxides such as molybdenum and tungsten oxides | 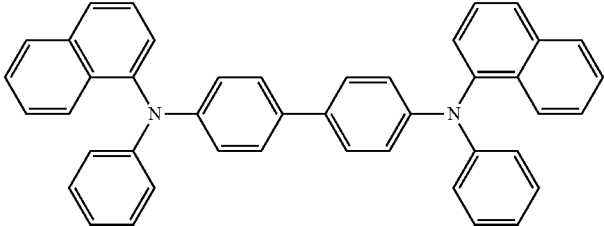 [SMILES: c1ccc(N(c2ccc(-c3ccc(N(c4ccccc4)c4cccc5ccccc45)cc3)cc2)c2cccc3ccccc23)cc1] | SID Symposium Digest, 37, 923 (2006) WO2009018009 |
| Semiconducting organic complexes | 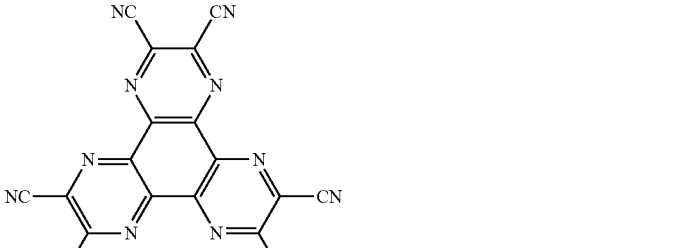 | US20020158242 |
| Metal organometallic complexes | 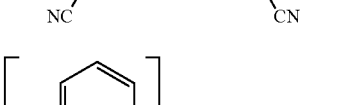 | US20060240279 |

TABLE 1-continued

| MATERIAL | EXAMPLES OF MATERIAL | PUBLICATIONS |
|---|---|---|
| Cross-linkable compounds | | US20080220265 |
| Hole transporting materials | | |
| Triarylamines (e.g., TPD, α-NPD) | | Appl. Phys. Lett. 51, 913 (1987) |
| | | U.S. Pat. No. 5,061,569 |
| | | EP650955 |

TABLE 1-continued
| MATERIAL | EXAMPLES OF MATERIAL | PUBLICATIONS |
|---|---|---|
| | 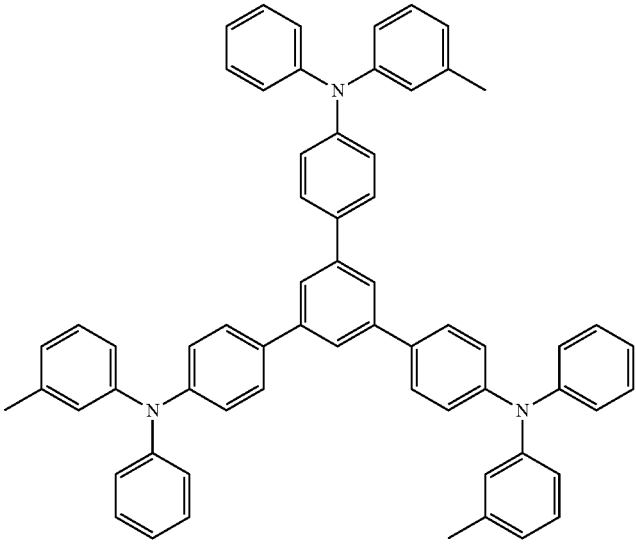 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |
| | 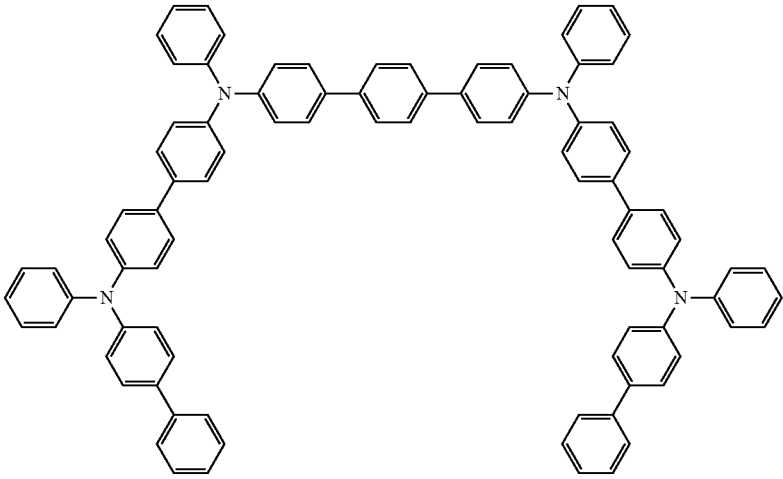 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |
| | 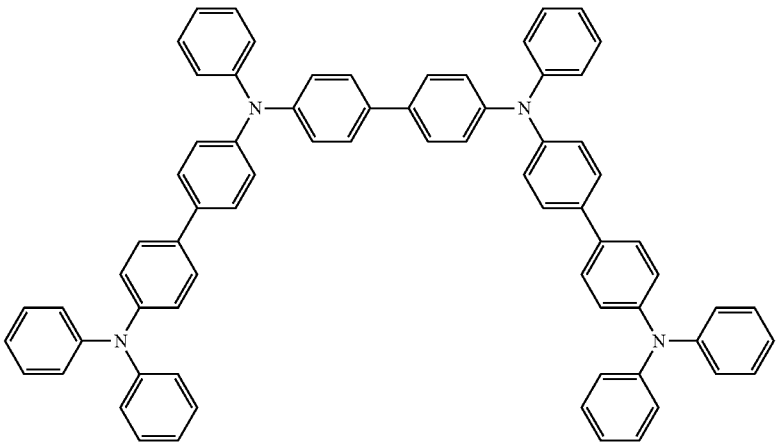 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett. 90, 183503 (2007) |

TABLE 1-continued

| MATERIAL | EXAMPLES OF MATERIAL | PUBLICATIONS |
| --- | --- | --- |
| Triarylamine on spirofluorene core | | Synth. Met. 91, 209 (1997) |
| Arylamine carbazole compounds | | Adv. Mater. 6, 677 (1994), US20080124572 |
| Triarylamine with (di)benzothiophene/ (di)benzofuran | | US20070278938, US20080106190 |
| Indolocarbazoles | | Synth. Met. 111, 421 (2000) |

US 8,748,011 B2
47                                                              48
TABLE 1-continued
| MATERIAL | EXAMPLES OF MATERIAL | PUBLICATIONS |
|---|---|---|
| Isoindole compounds | 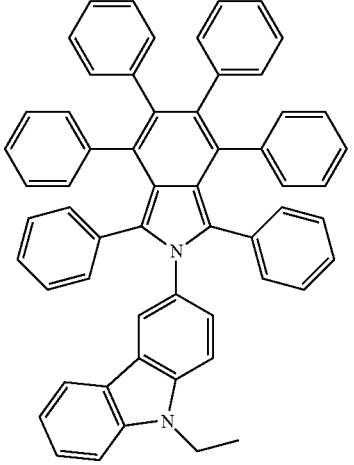 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 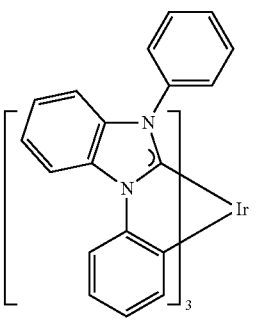 | US20080018221 |
| Phosphorescent OLED host materials | | |
| Red hosts | | |
| Arylcarbazoles | 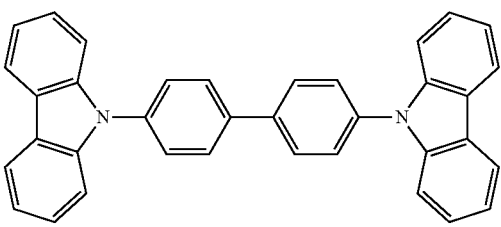 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| Metal 8-hydroxy-quinolates (e.g., Alq$_3$, BAlq) | 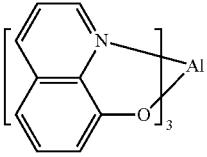 | Nature 395, 151 (1998) |
| | 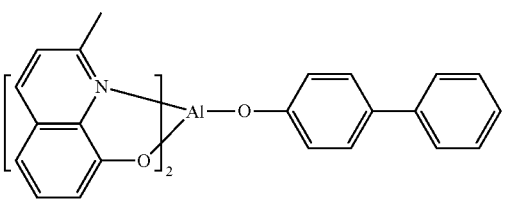 | US20060202194 |

TABLE 1-continued
| MATERIAL | EXAMPLES OF MATERIAL | PUBLICATIONS |
|---|---|---|
| | 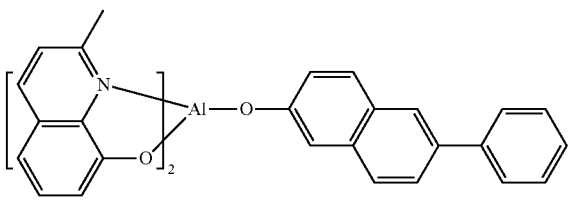 | WO2005014551 |
| | 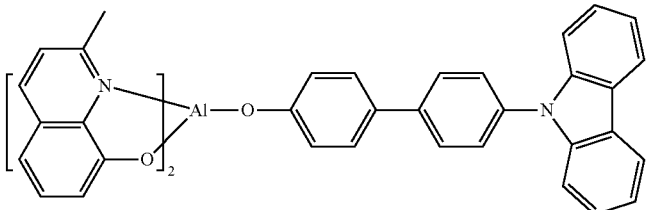 | WO2006072002 |
| Metal phenoxybenzothiazole compounds | 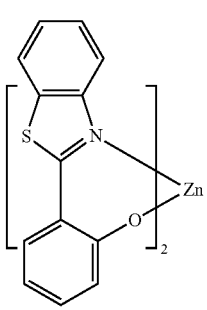 | Appl. Phys. Lett. 90, 123509 (2007) |
| Conjugated oligomers and polymers (e.g., polyfluorene) | 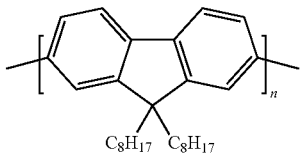 | Org. Electron. 1, 15 (2000) |
| Aromatic fused rings | 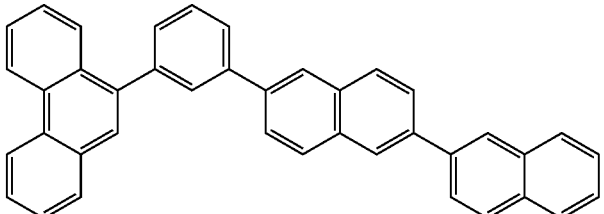 | WO2009066779, WO2009066778, WO2009063833, US20090045731, US20090045730, WO2009008311, US20090008605, U820090009065 |
| Zinc complexes | 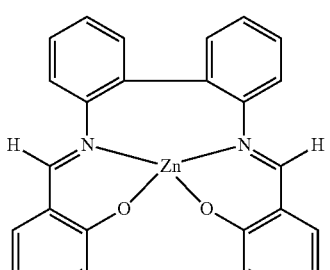 | WO2009062578 |
| Green hosts | | |

TABLE 1-continued
| MATERIAL | EXAMPLES OF MATERIAL | PUBLICATIONS |
|---|---|---|
| Arylcarbazoles | 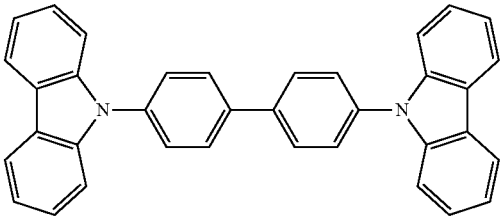 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 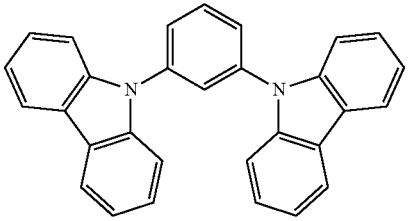 [SMILES: c1cc(-n2c3ccccc3c3ccccc32)cc(-n2c3ccccc3c3ccccc32)c1] | US20030175553 |
| | 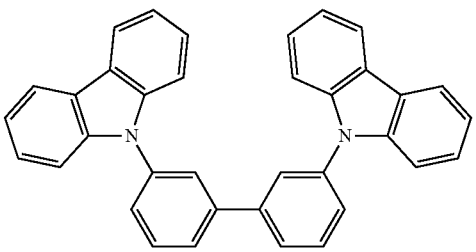 [SMILES: c1cc(-c2cccc(-n3c4ccccc4c4ccccc43)c2)cc(-n2c3ccccc3c3ccccc32)c1] | WO2001039234 |
| Aryltriphenylene compounds | 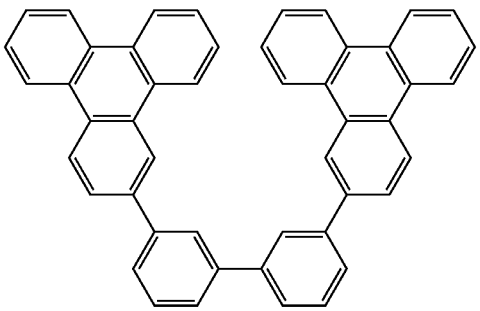 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 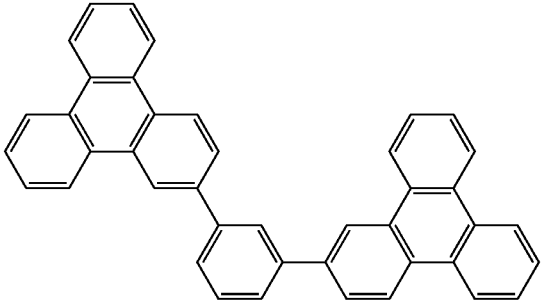 [SMILES: c1cc(-c2ccc3c4ccccc4c4ccccc4c3c2)cc(-c2ccc3c4ccccc4c4ccccc4c3c2)c1] | US20060280965 |
| | 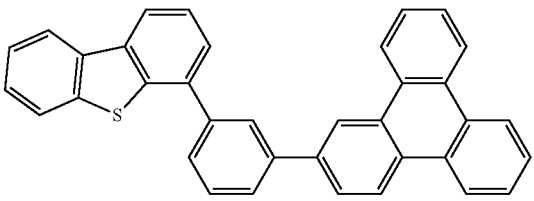 [SMILES: c1cc(-c2ccc3c4ccccc4c4ccccc4c3c2)cc(-c2cccc3c2sc2ccccc23)c1] | WO2009021126 |

TABLE 1-continued
| MATERIAL | EXAMPLES OF MATERIAL | PUBLICATIONS |
| --- | --- | --- |
| Donor acceptor type molecules | 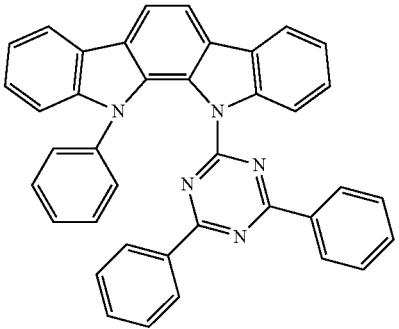 [SMILES: c1ccc(-c2nc(-c3ccccc3)nc(-n3c4ccccc4c4ccc5c6ccccc6n(-c6ccccc6)c5c43)n2)cc1] | WO2008056746 |
| Aza-carbazole/ DBT/DBF | 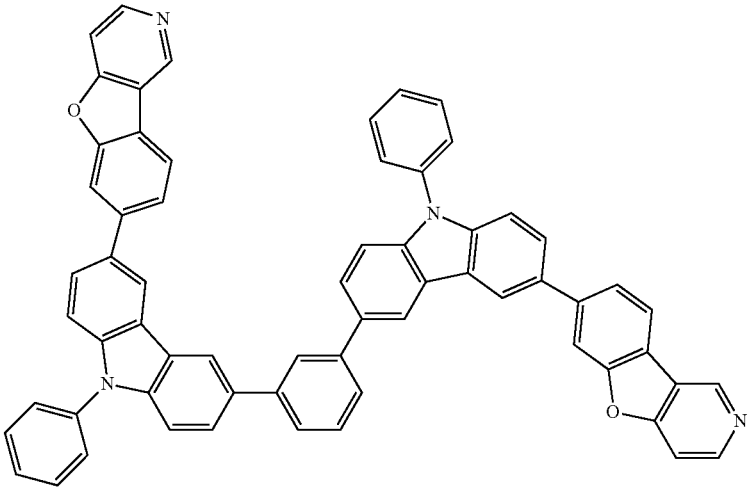 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| Polymers (e.g., PVK) | 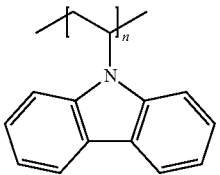 | Appl. Phys. Lett. 77, 2280 (2000) |
| Spirofluorene compounds | 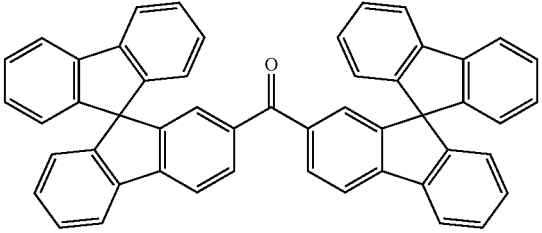 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 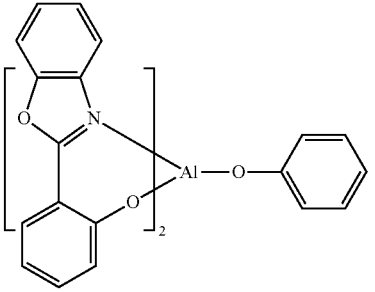 | WO2005089025 |

TABLE 1-continued
| MATERIAL | EXAMPLES OF MATERIAL | PUBLICATIONS |
|---|---|---|
| | 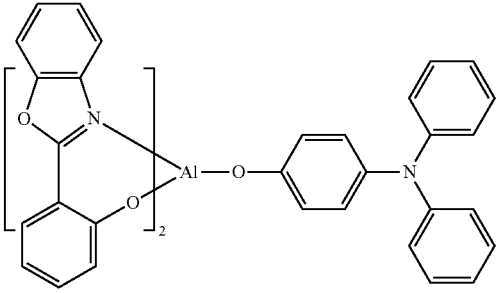 | WO2006132173 |
| | 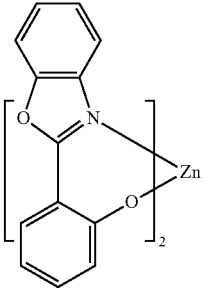 | JP200511610 |
| Spirofluorene-carbazole compounds | 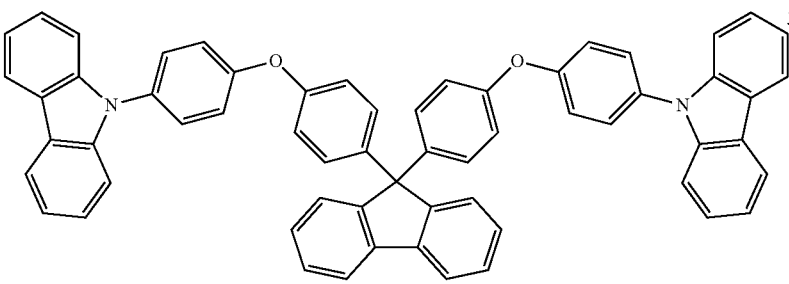 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |
| | 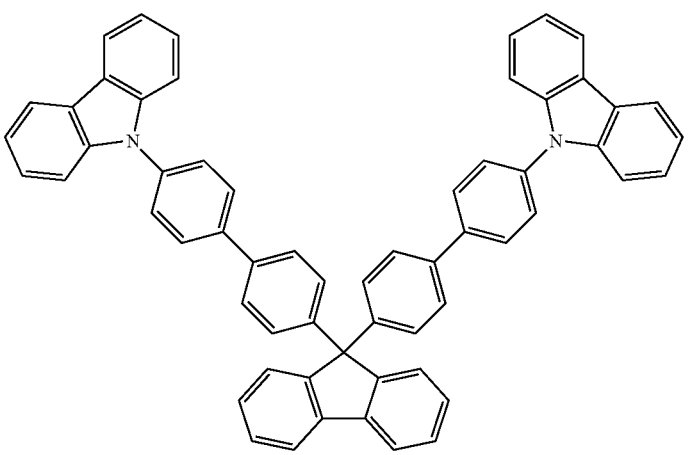 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolocarbazoles | 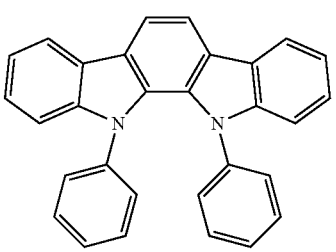 [SMILES: c1ccc(-n2c3ccccc3c3ccc4c5ccccc5n(-c5ccccc5)c4c32)cc1] | WO2007063796 |

TABLE 1-continued

| MATERIAL | EXAMPLES OF MATERIAL | PUBLICATIONS |
|---|---|---|
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |
| Metal phenoxypyridine compounds | | WO2005030900 |

TABLE 1-continued

| MATERIAL | EXAMPLES OF MATERIAL | PUBLICATIONS |
|---|---|---|
| Metal coordination complexes (e.g., Zn, Al with N^N ligands) | | US20040137268, US20040137267 |
| Blue hosts | | |
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |
| | | WO2009086028 |

| MATERIAL | EXAMPLES OF MATERIAL | PUBLICATIONS |
|---|---|---|
| | 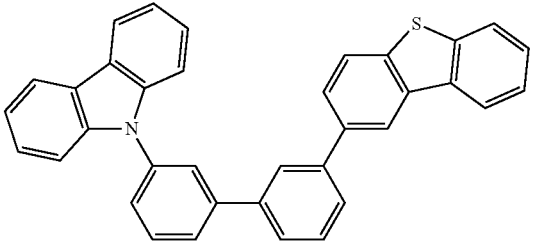 [SMILES: c1cc(-c2cccc(-n3c4ccccc4c4ccccc43)c2)cc(-c2ccc3sc4ccccc4c3c2)c1] | US20090030202, US20090017330 |
| Silicon aryl compounds | 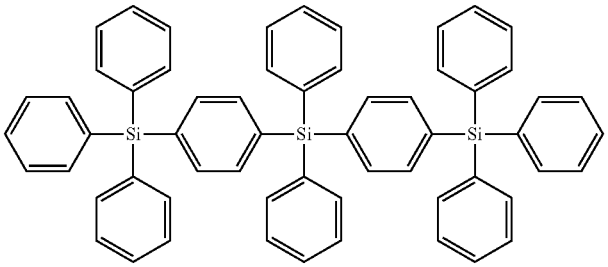 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 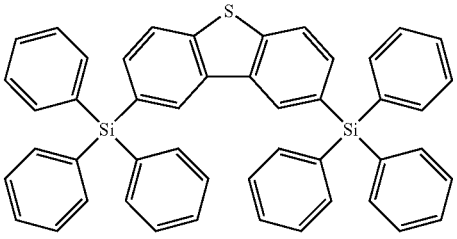 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 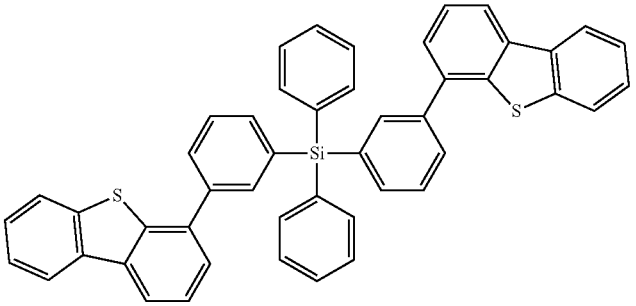 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 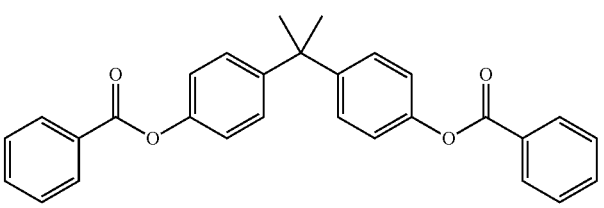 [SMILES: CC(C)(c1ccc(OC(=O)c2ccccc2)cc1)c1ccc(OC(=O)c2ccccc2)cc1] | WO2006100298 |
| High triplet metal organometallic complex | 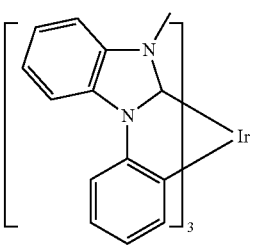 | U.S. Pat. No. 7,154,114 |

TABLE 1-continued

| MATERIAL | EXAMPLES OF MATERIAL | PUBLICATIONS |
| --- | --- | --- |
| Phosphorescent dopants | | |
| Red dopants | | |
| Heavy metal porphyrins (e.g., PtOEP) | | Nature 395, 151 (1998) |
| Iridium(III) organometallic complexes | | Appl. Phys. Lett. 78, 1622 (2001) |
| | | US2006835469 |
| | | US2006835469 |

TABLE 1-continued

| MATERIAL | EXAMPLES OF MATERIAL | PUBLICATIONS |
| --- | --- | --- |
| | | US20060202194 |
| | | US20060202194 |
| | | US20070087321 |
| | | US20070087321 |

TABLE 1-continued

| MATERIAL | EXAMPLES OF MATERIAL | PUBLICATIONS |
| --- | --- | --- |
| | [structure of Ir complex with isoquinoline ligand bearing C8H17 substituent, subscript 3] | Adv. Mater. 19, 739 (2007) |
| | [structure of Ir(acac) complex with phenyl-substituted dibenzo[f,h]quinoxaline ligand, subscript 2] | WO2009100991 |
| | [structure of Ir(acac) complex with benzotriazole-naphthyl ligand, subscript 2] | WO2008101842 |
| Platinum(II) organometallic complexes | [structure of Pt complex with phenylisoquinoline and acac ligands] | WO2003040257 |
| Osminum(III) complexes | [structure of Os(PPhMe2)2 complex with CF3-pyrazolyl-pyridine ligand, subscript 2] | Chem. Mater. 17, 3532 (2005) |

TABLE 1-continued

| MATERIAL | EXAMPLES OF MATERIAL | PUBLICATIONS |
| --- | --- | --- |
| Ruthenium(II) complexes | [Ru(PPhMe$_2$)$_2$ complex with $^t$Bu-pyrazolyl-isoquinoline ligand] | Adv. Mater. 17, 1059 (2005) |
| Rhenium (I), (II), and (III) complexes | [Re(CO)$_4$ complex with 8-hydroxyquinoline ligand] | US20050244673 |

Green dopants

| | | |
| --- | --- | --- |
| Iridium(III) organometallic complexes | [Ir(ppy)$_3$] and its derivatives | Inorg. Chem. 40, 1704 (2001) |
| | [Ir(ppy)$_2$(acac)] | US20020034656 |

TABLE 1-continued

| MATERIAL | EXAMPLES OF MATERIAL | PUBLICATIONS |
|---|---|---|
| | | U.S. Pat. No. 7,332,232 |
| | | US20090108737 |
| | | US20090039776 |
| | | U.S. Pat. No. 6,921,915 |

TABLE 1-continued

| MATERIAL | EXAMPLES OF MATERIAL | PUBLICATIONS |
|---|---|---|
| | | U.S. Pat. No. 6,687,266 |
| | | Chem. Mater. 16, 2480 (2004) |
| | | US20070190359 |
| | | US 20060008670<br>JP2007123392 |
| | | Adv. Mater. 16, 2003 (2004) |

TABLE 1-continued

| MATERIAL | EXAMPLES OF MATERIAL | PUBLICATIONS |
|---|---|---|
| | | Angew. Chem. Int. Ed. 2006, 45, 7800 |
| | | WO2009050290 |
| | | US20090165846 |
| | | US20080015355 |
| Monomer for polymeric metal organometallic compounds | | U.S. Pat. No. 7,250,226, U.S. Pat. No. 7,396,598 |

TABLE 1-continued

| MATERIAL | EXAMPLES OF MATERIAL | PUBLICATIONS |
| --- | --- | --- |
| Pt(II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |
| | | US20060263635 |

TABLE 1-continued

| MATERIAL | EXAMPLES OF MATERIAL | PUBLICATIONS |
|---|---|---|
| Cu complexes | | WO2009000673 |
| Gold complexes | | Chem. Commun. 2906 (2005) |
| Rhenium(III) complexes | | Inorg. Chem. 42, 1248 (2003) |
| Deuterated organometallic complexes | | US20030138657 |

TABLE 1-continued

| MATERIAL | EXAMPLES OF MATERIAL | PUBLICATIONS |
|---|---|---|
| Organometallic complexes with two or more metal centers | | US20030152802 |
| | | U.S. Pat. No. 7,090,928 |
| Blue dopants | | |
| Iridium(III) organometallic complexes | | WO2002002714 |
| | | WO2006009024 |
| | | US20060251923 |

TABLE 1-continued

| MATERIAL | EXAMPLES OF MATERIAL | PUBLICATIONS |
| --- | --- | --- |
| | | U.S. Pat. No. 7,393,599, WO2006056418, US20050260441, WO2005019373 |
| | | U.S. Pat. No. 7,534,505 |
| | | U.S. Pat. No. 7,445,855 |
| | | US20070190359, US20080297033 |
| | | U.S. Pat. No. 7,338,722 |
| | | US20020134984 |

| MATERIAL | EXAMPLES OF MATERIAL | PUBLICATIONS |
|---|---|---|
| | 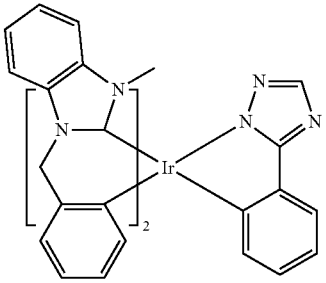 | Angew. Chem. Int. Ed. 47, 1 (2008) |
| | 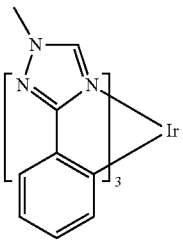 | Chem. Mater. 18, 5119 (2006) |
| | 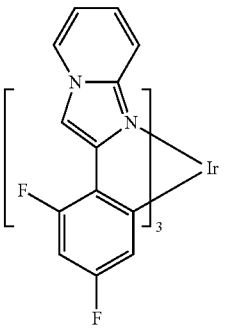 | Inorg. Chem. 46, 4308 (2007) |
| | 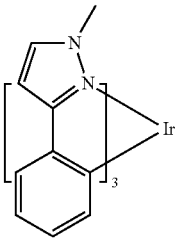 | WO2005123873 |
| | 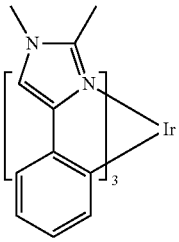 | WO2005123873 |
| | 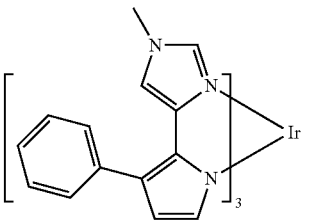 | WO2007004380 |

TABLE 1-continued

| MATERIAL | EXAMPLES OF MATERIAL | PUBLICATIONS |
|---|---|---|
| | [Ir complex structure] | WO2006082742 |
| Osmium(II) complexes | [Os complex structure] | U.S. Pat. No. 7,279,704 |
| | [Os(PPh$_3$) complex structure] | Organometallics 23, 3745 (2004) |
| Gold complexes | [Ph$_2$P–Au–Cl dimer structure] | Appl. Phys. Lett. 74, 1361 (1999) |
| Platinum(II) complexes | [Pt complex structure] | WO2006098120, WO2006103874 |

Exciton/hole blocking layer materials

TABLE 1-continued
| MATERIAL | EXAMPLES OF MATERIAL | PUBLICATIONS |
| --- | --- | --- |
| Bathocuprine compounds (e.g., BCP, BPhen) | 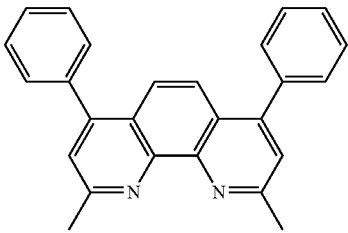 [SMILES: Cc1cc(-c2ccccc2)c2ccc3c(-c4ccccc4)cc(C)nc3c2n1] | Appl. Phys. Lett. 75, 4 (1999) |
| | 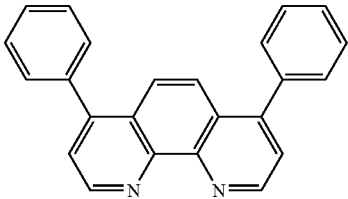 [SMILES: c1ccc(-c2ccnc3c2ccc2c(-c4ccccc4)ccnc23)cc1] | Appl. Phys. Lett. 79, 449 (2001) |
| Metal 8-hydroxy-quinolates (e.g., BAlq) | 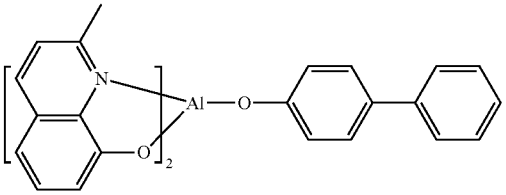 | Appl. Phys. Lett. 81, 162 (2002) |
| 5-member ring electron deficient heterocycles such as triazole, oxadiazole, imidazole, benzoimidazole | 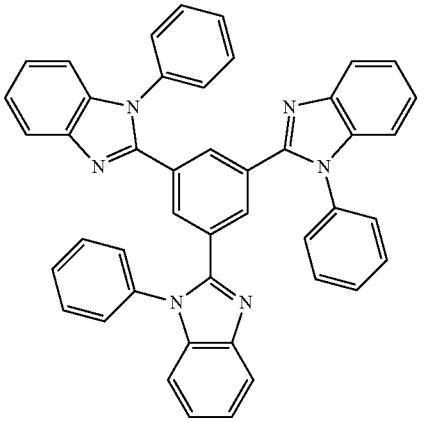 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 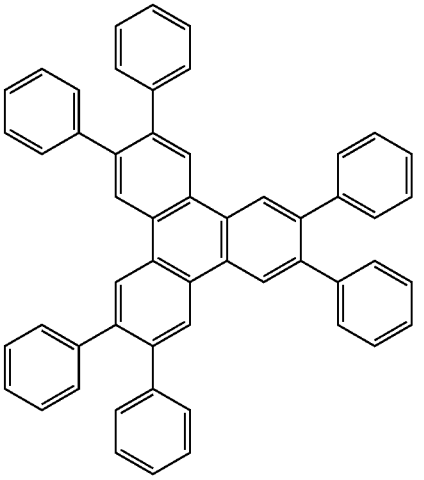 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |

TABLE 1-continued
| MATERIAL | EXAMPLES OF MATERIAL | PUBLICATIONS |
|---|---|---|
| Fluorinated aromatic compounds | 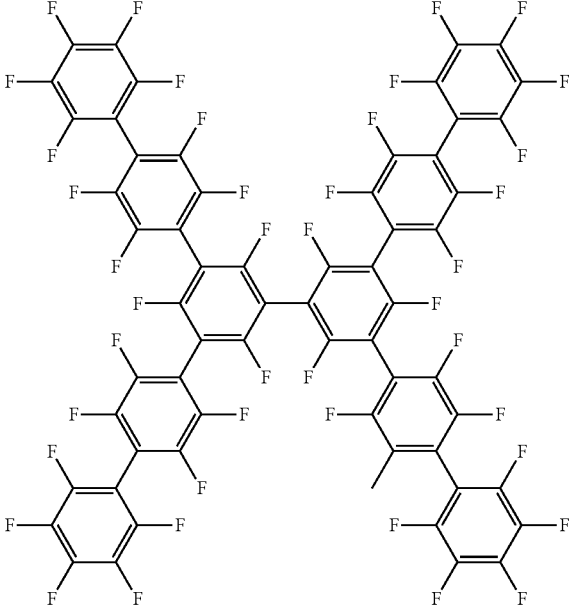 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 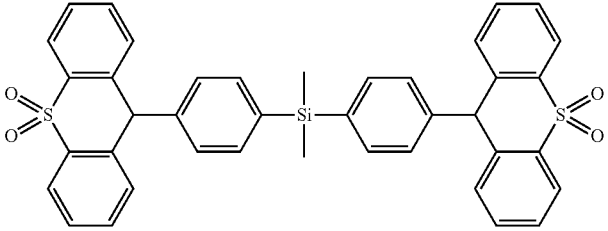 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Electron transporting materials | | |
| Anthracene-benzoimidazole compounds | 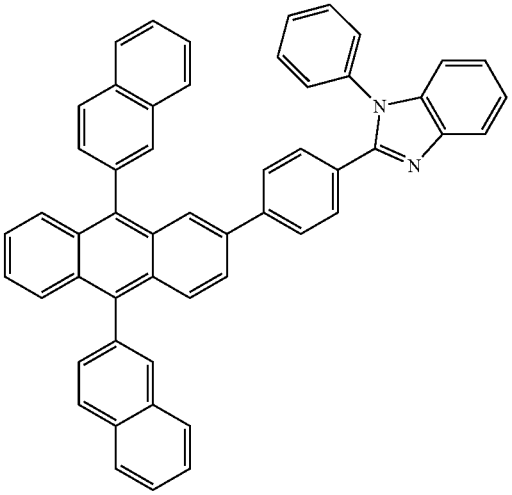 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |

TABLE 1-continued

| MATERIAL | EXAMPLES OF MATERIAL | PUBLICATIONS |
| --- | --- | --- |
| | | US20090179554 |
| Aza triphenylene derivatives | | US20090115316 |
| Anthracene-benzothiazole compounds | | Appl. Phys. Lett. 89, 063504 (2006) |
| Metal 8-hydroxy-quinolates (e.g., Alq$_3$, Zrq$_4$) | | Appl. Phys. Lett. 51, 913 (1987)<br>U.S. Pat. No. 7,230,107 |
| Metal hydroxybenzo-quinolates | | Chem. Lett. 5, 905 (1993) |
| Bathocuprine compounds such as BCP, BPhen, etc | | Appl. Phys. Lett. 91, 263503 (2007) |

TABLE 1-continued

| MATERIAL | EXAMPLES OF MATERIAL | PUBLICATIONS |
|---|---|---|
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |
| Silole compounds | | Org. Electron. 4, 113 (2003) |
| Arylborane compounds | | J. Am. Chem. Soc. 120, 9714 (1998) |

TABLE 1-continued

| MATERIAL | EXAMPLES OF MATERIAL | PUBLICATIONS |
|---|---|---|
| Fluorinated aromatic compounds | 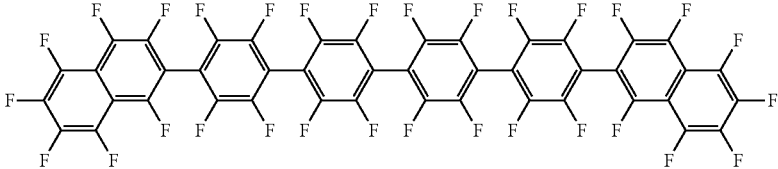 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 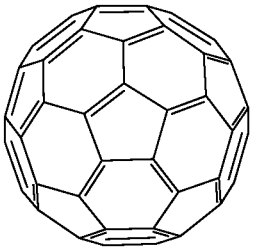 [SMILES: c1cc2c3ccc4c5ccc6c7ccc8c9ccc%10c1c1c2c2c3c4c3c5c6c4c7c8c5c9c%10c1c1c2c3c4c51] | US20090101870 |
| Triazine complexes | 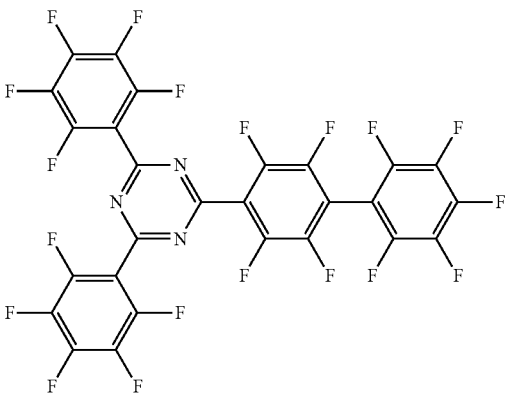 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |
| Zn (N^N) complexes | 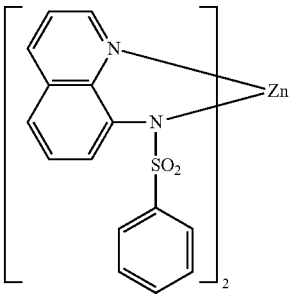 | U.S. Pat. No. 6,528,187 |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

EXPERIMENTAL

Chemical abbreviations used throughout this document are as follows: DMF is dimethylformamide, Et$_3$N is triethylamine, PPh$_3$ is tripheynylphosphine, P(i-Pr)$_3$ is triisopropylphosphine, EtOAc is ethyl acetate, THF is tetrahydrofuran, DMSO is dimethylsulfoxide, DCM is dichloromethane, dba is dibenzylideneacetone, HMPA is hexamethylphosphoramide, S-Phos is dicyclohexyl(2',6'-dimethoxy[1,1'-biphenyl]-2-yl)-phosphine.

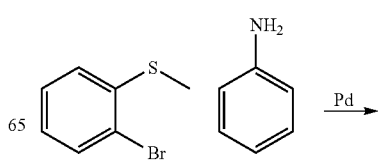

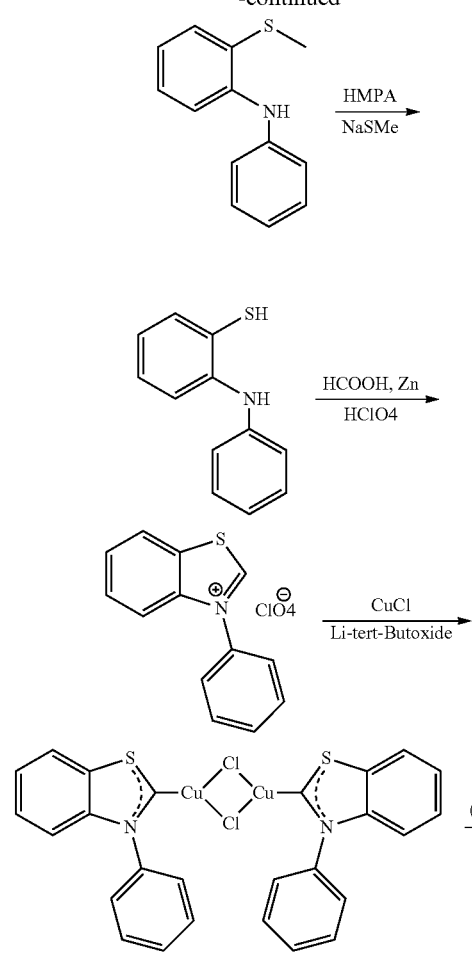

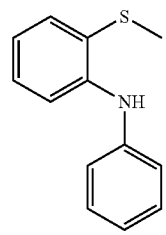

(2-bromophenyl)(methyl)sulfane (25 g, 123 mmol), Pd$_2$dba$_3$ (6.75 g, 7.38 mmol), S-Phos (6.06 g, 14.77 mmol) and sodium tert-butoxide (17.74 g, 185 mmol) were placed in a dry 3 neck flask under N$_2$. The reaction mixture was vacuum evacuated and back filled with N$_2$ three times. Aniline (22.93 g, 246 mmol) and 500 mL toluene were added to the reaction mixture. The reaction mixture was refluxed for 18 hours. The crude reaction mixture was run through a silica gel plug and eluted with toluene. The toluene portion was concentrated down and subjected to a silica gel column by using 3-5% DCM in hexanes to yield desired product. (24 g, 111 mmol, 91%)

Synthesis of 2-(phenylamino)benzenethiol

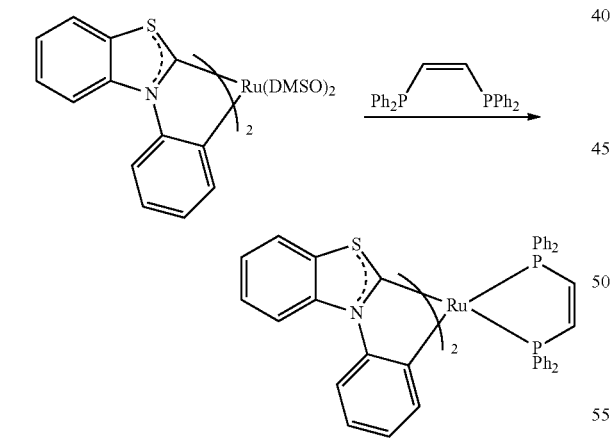

A 250 mL round bottom flask was charged with sodium methanethiolate (5.18 g, 73.8 mmol), 2-(methylthio)-N-phenylaniline (13.25 g, 61.5 mmol) and hexamethyiphosphoramide (HMPA) (100 mL). The reaction mixture was heated up to 140° C. for 7 hours. The reaction was cooled to room temperature and 100 mL of 1N HCl was added. The reaction mixture was extracted with 3×100 mL ethyl acetate, the organic portion was washed with 3×50 mL brine, dried over sodium sulfate and evaporated to yield the desired compound. (12 g, 97%)

Synthesis of benzothioazole carbene ligand precursor

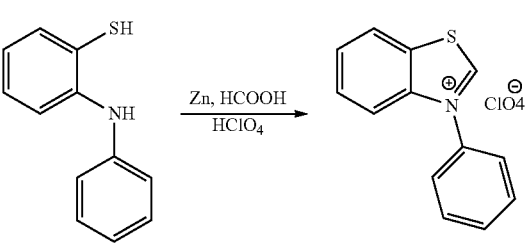

A 250 mL round bottom flask was charged with zinc dust (2.339 g, 35.8 mmol), 2-(phenylamino)benzenethiol (12 g, 59.6 mmol) and formic acid (100 mL). The reaction mixture was refluxed under N$_2$ for six hours. The reaction mixture was filtered off to remove insoluble material. Perchloric acid (35.9 mL, 59.9 mmol) was added to the filtrate and stirred for 20 minutes. 200 mL of water was added and the precipitation Synthesis of 2-(methylthio)-N-phenylaniline

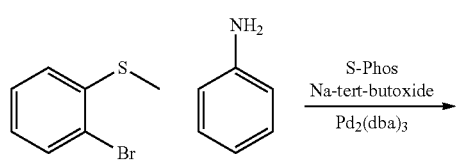

was collected. The precipitate was washed with H₂O and ether to yield desired product (13.6 g, 73 N.

Synthesis of Dichloro Copper Dimer

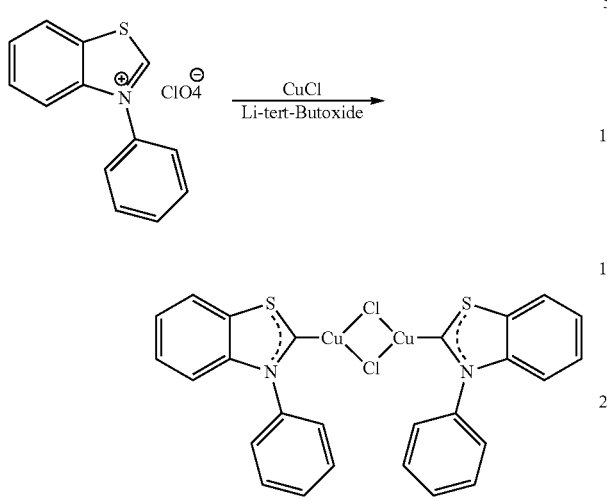

A 500 mL round bottom flask was charged with CuCl (3.9 g, 39.4 mmol), lithium tert-butoxide (3.15 g, 39.4 mmol) and anhydrous THF (400 mL). The reaction mixture was stirred inside a glove box over night. Subsequently, the perchlorate salt synthesized above (2.31 g, 7.41 mmol) was added to the reaction mixture and stirred over night. The reaction mixture was removed from the glove box and filtered; the filtrate was concentrated to dryness and re-suspended in dichloromethane. The suspension was filtered and the filtrate was concentrated to dryness to yield the desired compound. (1.68 g, 76%)

Synthesis of Ruthenium Carbene DMSO Complexes

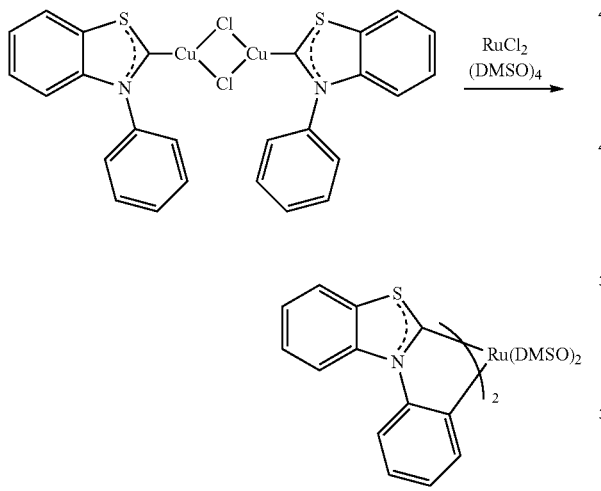

Dichloro copper dimer (1 g, 1.606 mmol) from the previous step is mixed with RuCl₂(DMSO)₄ (0.777 g, 1.606 mmol) in 2-ethoxyethanol. The reaction mixture is vacuum evacuated and back filled with N₂ three times. The reaction mixture was heated to reflux for 1 hour. The reaction mixture was evaporated to dryness under vacuum. The residue was purified by column chromatography to yield the desired compound.

Synthesis of Ruthenium Benzothioazole Carbene Complexes

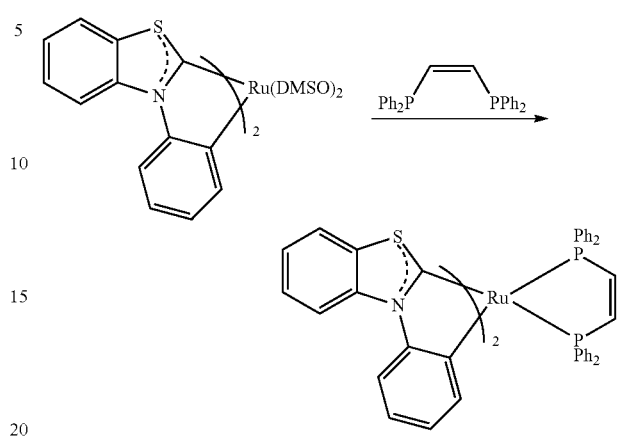

The ruthenium carbene DMSO complex from the previous step is mixed with excess phosphine ligand and tridecane. The reaction mixture is heated to reflux for 1 hour. The reaction mixture is evaporated to dryness under vacuum. The residue is purified by column chromatography to yield the desired compound.

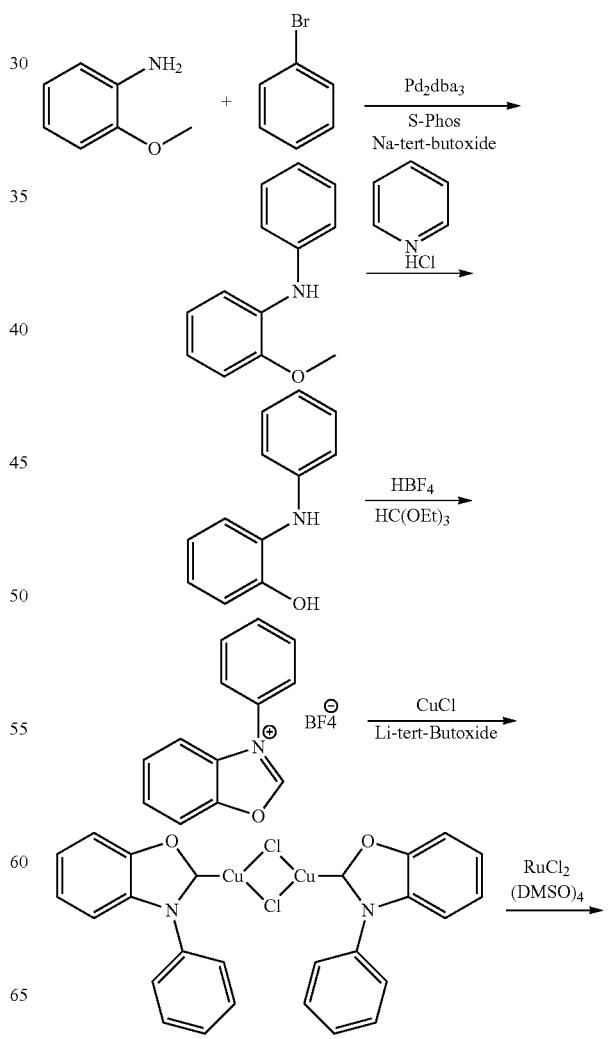

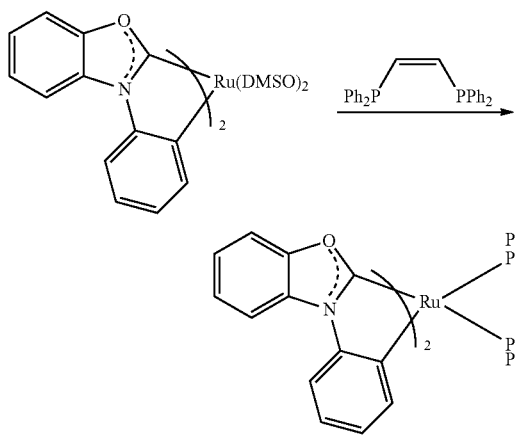

Synthesis of 2-methoxy-N-phenylaniline

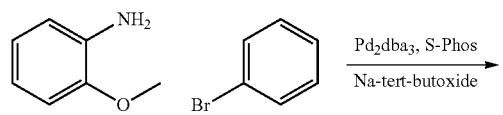

A 1 L three neck flask was charged with 2-methoxyaniline (17.65 g, 143 mmol), bromobenzene (15 g, 96 mmol), Pd$_2$(dba)$_3$ (1.75 g, 1.91 mmole), S-Phos (1.56 g, 3.82 mmol), sodium tert-butoxide (18.36 g, 101 mmol) and 400 mL of xylene. The reaction mixture was refluxed for 4 hours. The product was isolated by column chromatography (5% EtOAc in hexanes) to yield the desired product. (18 g, 94%)

Synthesis of 2-(phenylamino)phenol

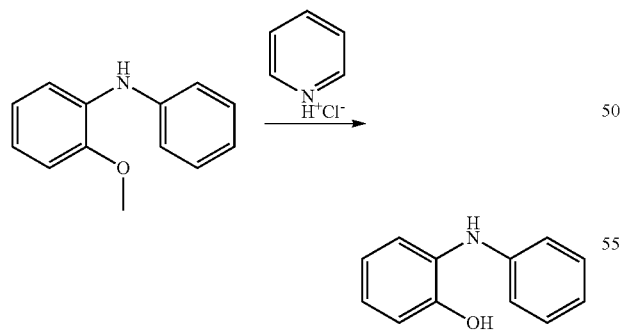

A 1 L three neck flask was charged with pyridinium chloride (52.2 g, 452 mmol) and 2-methoxy-N-phenylaniline (9 g, 45.2 mmol). The reaction mixture was heated to 200° C. for 4 hours. The reaction mixture was poured into 5% HCl (200 mL) and extracted with EtOAc (3×300 mL). The organic portion was combined and purified by column chromatography (100% DCM) to yield the desired product. (6.5 g, 77%)

Synthesis of Benzoxazole Salt

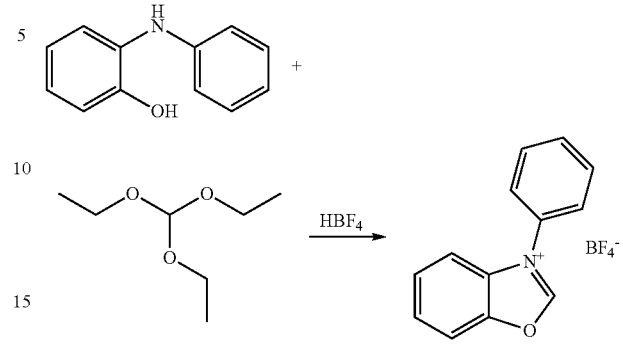

Hydrogen tetrafluoroborate (6.79 mL, 48% w/w) was added drop wise to a solution of 2-(phenylamino)phenol (9 g, 48.6 mmol) in 30 mL methanol. After 30 minutes of stirring, the solvent was removed under vacuum and (EtO)$_3$CH (30 mL) was added. The resulting solution was stirred at room temperature under N$_2$ overnight to give a white suspension. The solid was filtered and washed with diethyl ether to give 10 g of product (72%).

Synthesis of Ruthenium Benzoxazole Carbene Complexes

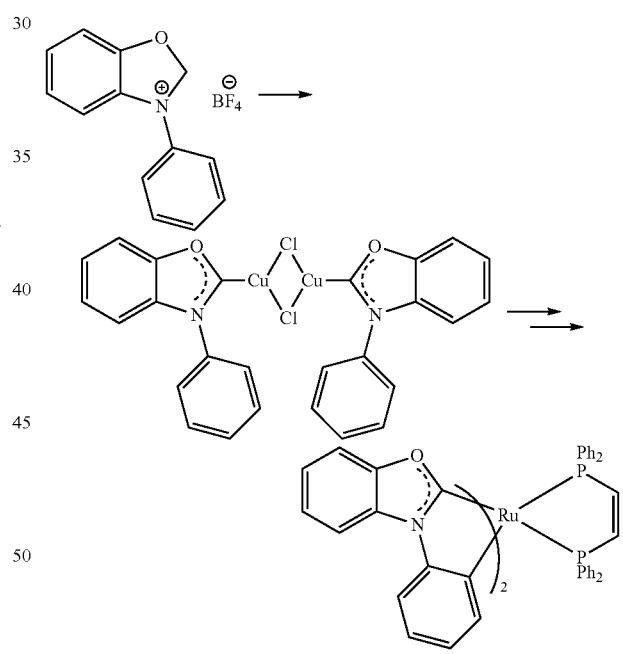

The benzoxazole carbene complex is synthesized in a manner analogous to the benzothiazole complex described above.

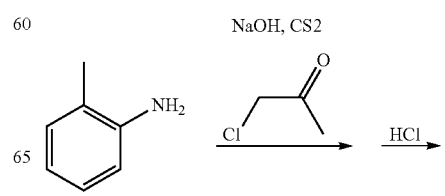

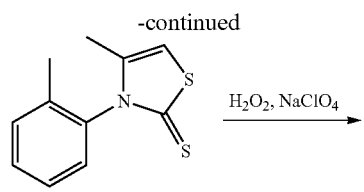

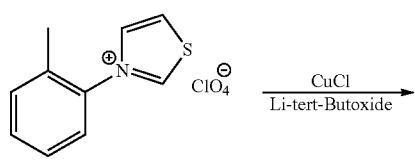

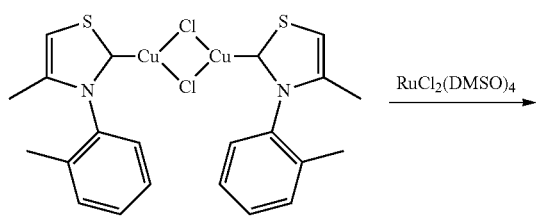

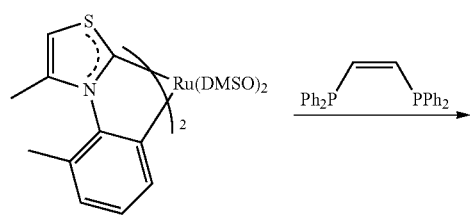

Synthesis of 4-methyl-3-(o-tolyl)thiazole-2(3H)-thione

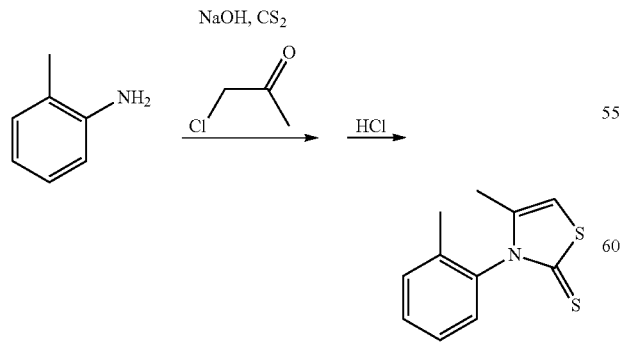

A solution of 2-methyl aniline (10.71 g, 100 mmol) in DMSO (50 mL) was treated with 20N aqueous NaOH (5 mL, 100 mmol) at room temperature. The mixture was cooled to 0° C. and CS$_2$ (7.61 g, 100 mmol) was added. Upon stirring for 1 hour at room temperature, a change of color from dark-red to orange was observed. The solution was then cooled to 0° C. and chloroacetone (9.25 g, 100 mmol) was added. After stirring for 3 hours at room temperature, water (100 mL) was added and the mixture was stirred for an additional 10 minutes at 0° C. The precipitate was filtered and successively washed with water and ethanol. The crude product was suspended in 95% ethanol (100 mL), and 36% HCl (50 mL) was added and the mixture was heated to reflux for 1 hour. After cooling to room temperature, the precipitate was filtered to yield the desired product. (8.7 g, 38%)

Synthesis of Thioazole Salt

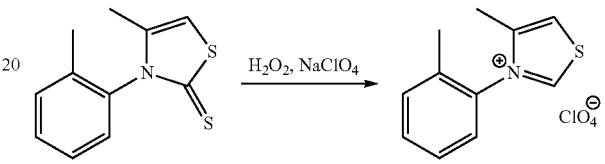

The thione from the previous step (4 g, 18.07 mmol) was dissolved in aceteic acid (100 mL) and 30% hydrogen peroxide (4.7 mL) was added. After stirring the resulting yellow solution for 30 mins at room temperature, the solvent was removed in vacuo. The residue was dissolved in methanol (40 mL) and treated with a solution of NaClO$_4$ (9.29 g, 75.9 mmol) in a 2:1 mixture of methanol/water. After stirring for a few minutes at 0° C., a yellow solid precipitated. The crude product was filtered and washed with water (50 mL) and ethanol (100 mL) to yield the desired compound.

Synthesis of Ruthenium Thioazole Carbene Phosphine Complexes

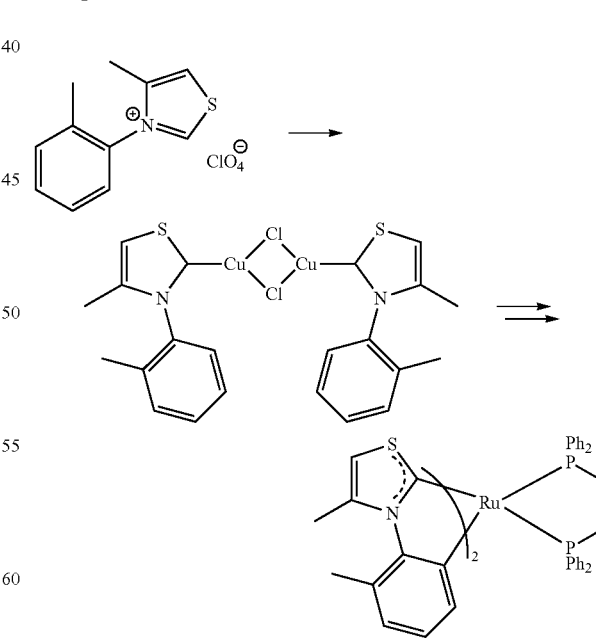

The thiazole carbene complex is synthesized in a manner analogous to the benzothiazole complex described above.

The invention claimed is:

1. A compound comprising a metal complex having the formula II:

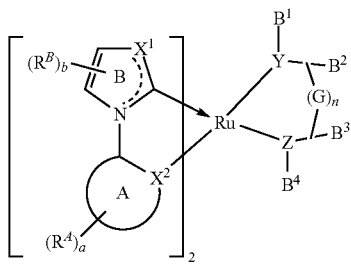

wherein auxiliary ligand

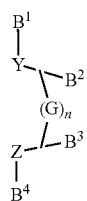

bears no charge;
wherein the Ru bears a +2 charge;
wherein the metal complex has an overall 0 charge;
wherein ring B is connected to the Ru through a carbene bond;
wherein ring A is aromatic and selected from the group consisting of a 5- or 6-membered carbocyclic or heterocyclic group;
each $R^A$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein $R^A$ may be optionally linked to form a ring fused to ring A and wherein the fused ring is optionally substituted;
a is 0 to 4;
$X^1$ is selected from N—R', O, and S;
$X^2$ is selected from C and N;
each $R^B$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein $R^B$ may be optionally linked to form a ring fused to ring B and wherein the fused ring is optionally substituted;
b is 0 to 4;
Y and Z are independently selected from the group consisting of C, N and P;
$B^1$, $B^2$, $B^3$, $B^4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
$B^1$ and $B^2$ are optionally linked to form a 5- or 6-membered cyclic group having from 0 to 4 ring heteroatoms, an 8- to 10-membered fused bicyclic group having from 0 to 4 ring heteroatoms, wherein the 5- or 6-membered cyclic group having from 0 to 4 ring heteroatoms, and the 8- to 10-membered fused bicyclic group having from 0 to 4 ring heteroatoms may be optionally substituted with one or more substituents independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
$B^3$ and $B^4$ are optionally linked to form a 5- or 6-membered cyclic group having from 0 to 4 ring heteroatoms, an 8- to 10-membered fused bicyclic group having from 0 to 4 ring heteroatoms, wherein the 5- or 6-membered cyclic group having from 0 to 4 ring heteroatoms, and the 8- to 10-membered fused bicyclic group having from 0 to 4 ring heteroatoms may be optionally substituted with one or more substituents independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
G is selected from the group consisting of alkyl and alkenyl having from 1 to 5 carbon atoms, wherein a first end of G is bonded to Y or $B^2$, and a second end of G is bonded to Z or $B^3$;
n is 0 or 1; wherein when n is 0, G is absent;
wherein R' is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
wherein:
(a) at least one of Y and Z is a carbine carbon,
(b) Y is P, Z is P, n=1, and G is alkenyl, or
(c) Y is P, Z is P, n=1, is alkyl, and $B^1$ is selected from the group consisting of hydrogen, deuterium, halide, alkyl, cycloalkyl, heteroalkyl, arylakyl, alkoxy, aryloxy, amino, silyl, alkenyl, cycloalkenyl, heteroalkenyl, alkynyl, heteroaryl, acyl, carbonyl, carboxylic, acids, ester, nitrile, isonitrile, sulfinyl, sulfonyl, phosphino, and combinations thereof.

2. The compound of claim 1, wherein the metal complex has the formula III:

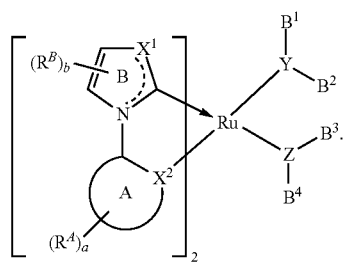

3. The compound of claim 2, wherein the metal complex has the formula VI:

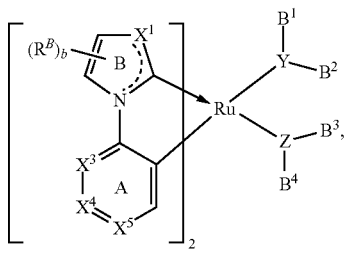

wherein:
$X^3$ is selected from the group C—$R^1$ and N;
$X^4$ is selected from the group C—$R^2$ and N;
$X^5$ is selected from the group C—$R^3$ and N; and
wherein $R^1$, $R^2$, and $R^3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

4. The compound of claim 3, wherein the metal complex has the formula VII:

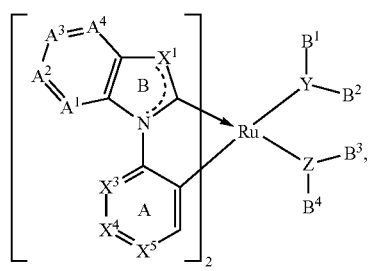

wherein $A^1$, $A^2$, $A^3$, and $A^4$ are independently selected from the group consisting of C—R' and N.

5. The compound of claim 4, wherein the metal complex has the formula VIII:

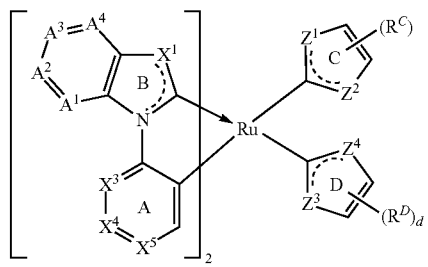

wherein $R^C$ and $R^D$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein c is 0 to 4;
wherein d is 0 to 4;
wherein $R^C$ may be optionally linked to form a ring fused to ring C and wherein the fused ring is optionally substituted;
wherein $R^D$ may be optionally linked to form a ring fused to ring D and wherein the fused ring is optionally substituted; and
wherein $Z^1$, $Z^2$, $Z^3$, and $Z^4$ are independently selected from N—R', S, and O.

6. The compound of claim 5, wherein the metal complex has the formula IX:

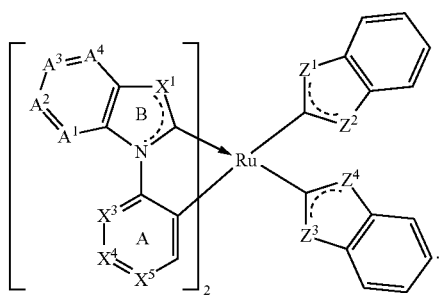

7. The compound of claim 6, wherein the metal complex is selected from the group consisting of:

Compound 1

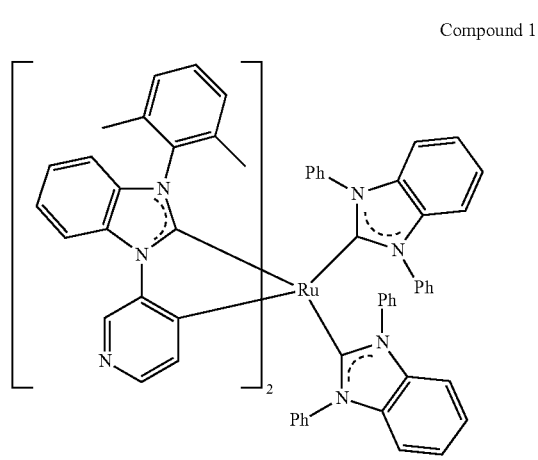

Compound 2

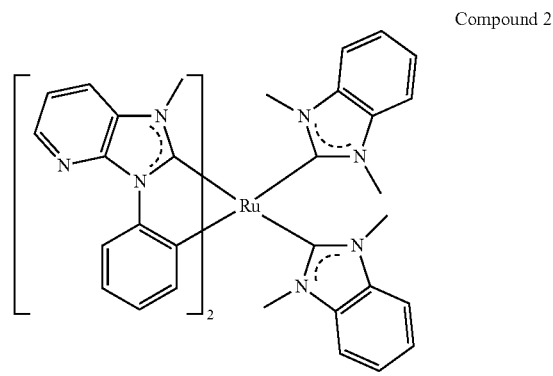

Compound 3
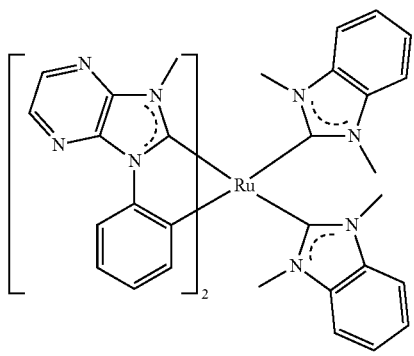
Compound 4
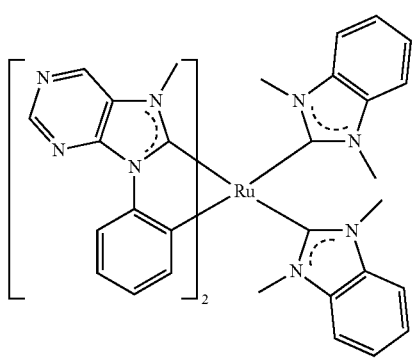
Compound 5
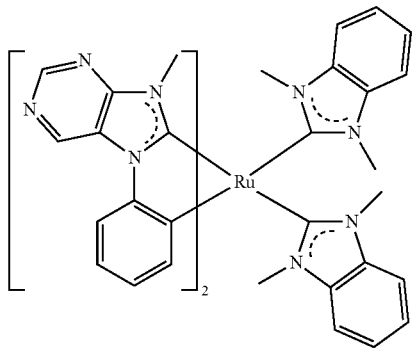
Compound 6
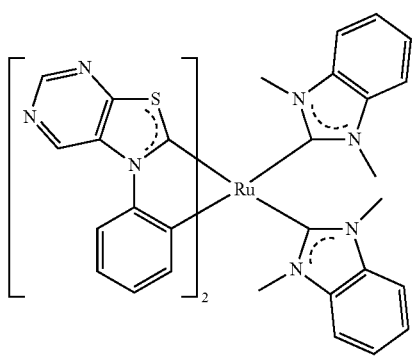
Compound 7
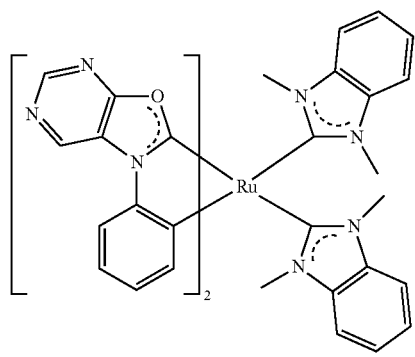
Compound 8
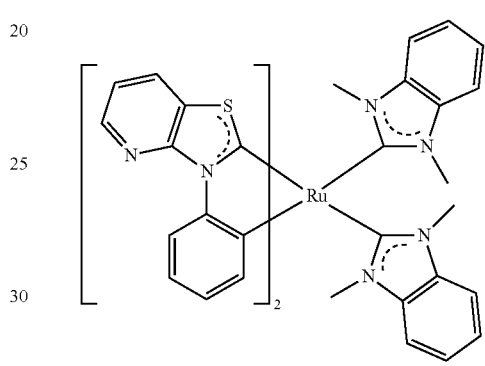
Compound 9
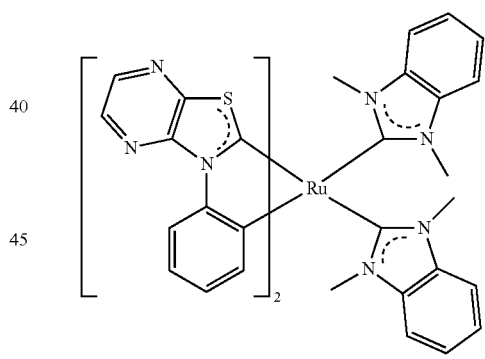
Compound 10
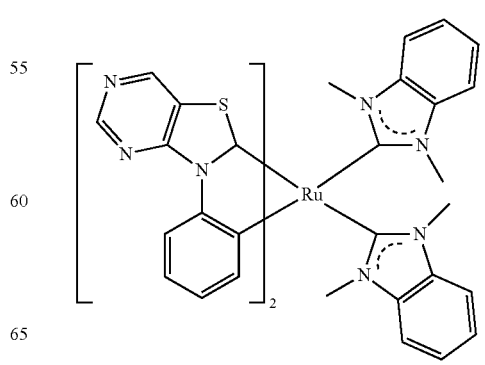

Compound 11

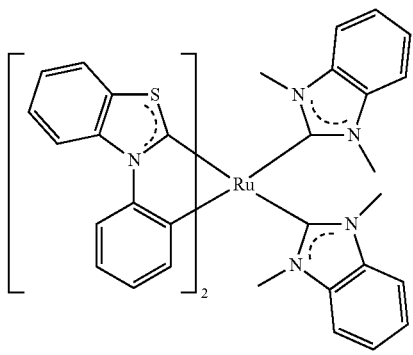

Compound 12

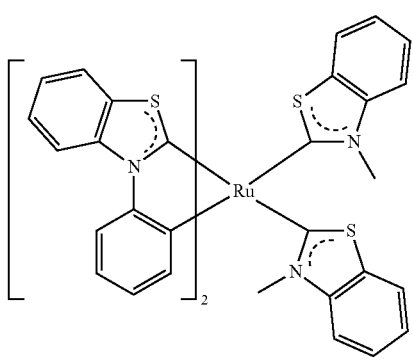

Compound 13

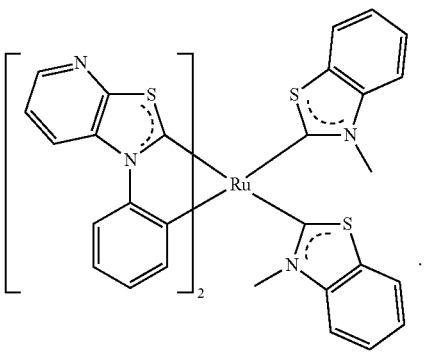

8. The compound of claim 1, wherein the complex has the formula IV:

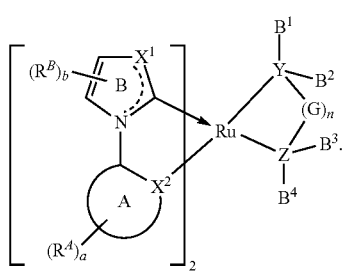

9. The compound of claim 8, wherein the metal complex has the formula X:

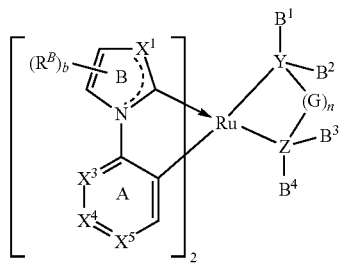

wherein:
$X^3$ is selected from the group C—$R^1$ and N;
$X^4$ is selected from the group C—$R^2$ and N;
$X^5$ is selected from the group C—$R^3$ and N; and
wherein $R^1$, $R^2$, and $R^3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfonyl, sulfinyl, sulfonyl, phosphino, and combinations thereof.

10. The compound of claim 9, wherein the metal complex has the formula XI:

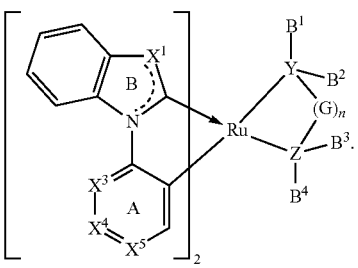

11. The compound of claim 10, wherein the metal complex has the formula XII:

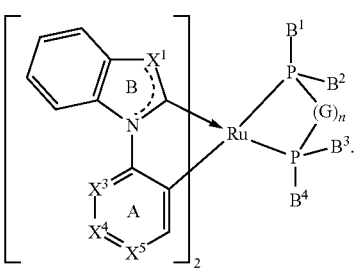

12. The compound of claim 11, wherein the metal complex has the formula XIII:

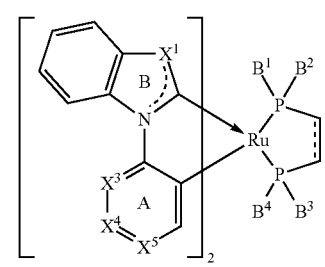

wherein:

the dashed line on the phosphine ligand represents an optional bond.

13. The compound of claim 12, wherein the metal complex is selected from the group consisting of:

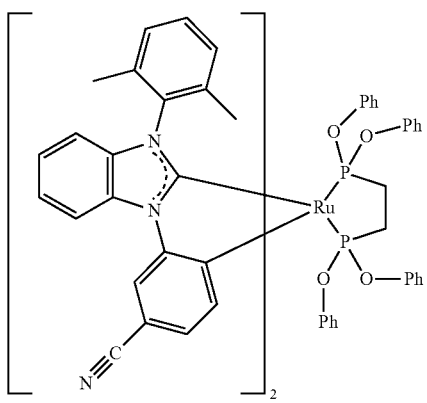

Compound 14

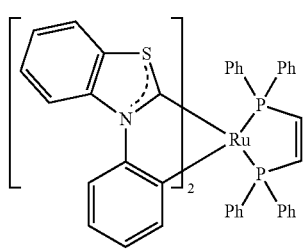

Compound 15

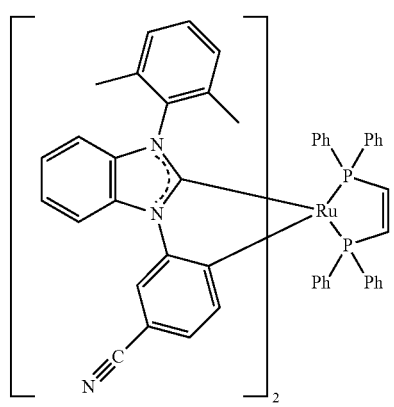

Compound 16

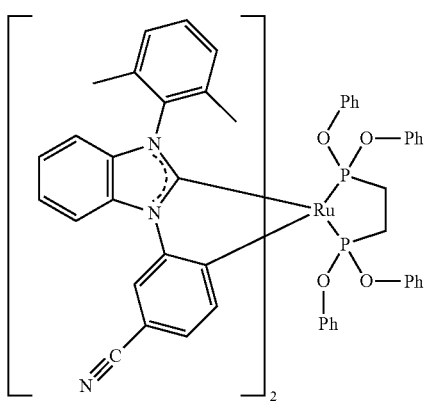

Compound 17

-continued

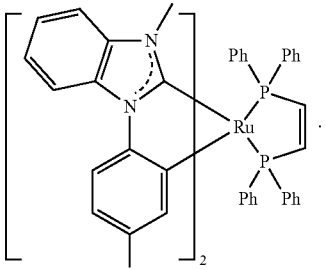

Compound 18

14. The compound of claim 1, wherein the metal complex has the formula V:

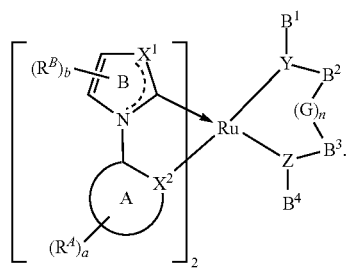

15. The compound of claim 14, wherein the metal complex has the formula XIV:

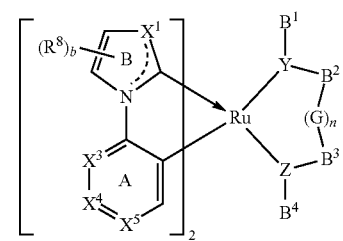

wherein:
$X^3$ is selected from the group C—$R^1$ and N;
$X^4$ is selected from the group C—$R^2$ and N;
$X^5$ is selected from the group C—$R^3$ and N; and
wherein $R^1$, $R^2$, and $R^3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

16. The compound of claim 15, wherein the metal complex has the formula XV:

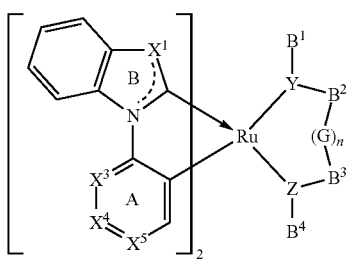

17. The compound of claim 16, wherein the metal complex has the formula XVI:

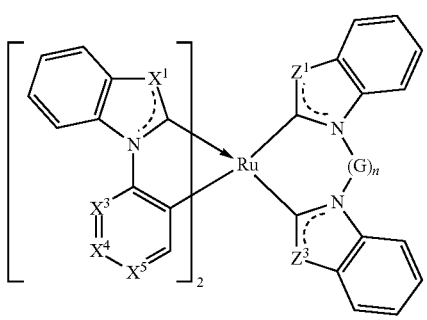

wherein:
Z$^1$ and Z$^3$ are independently selected from N—R', S, and O.

18. The compound of claim 17, wherein the metal complex is selected from the group consisting of:

Compound 19

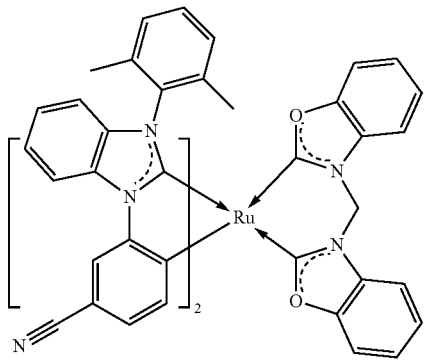

Compound 20

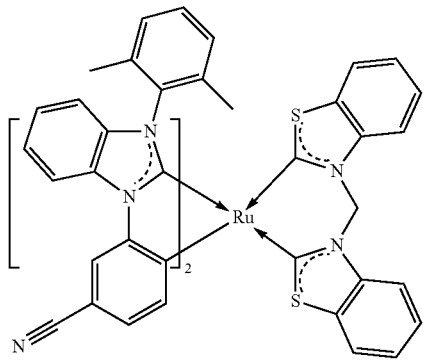

Compound 21

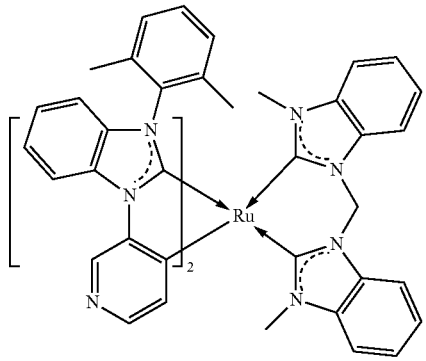

Compound 22

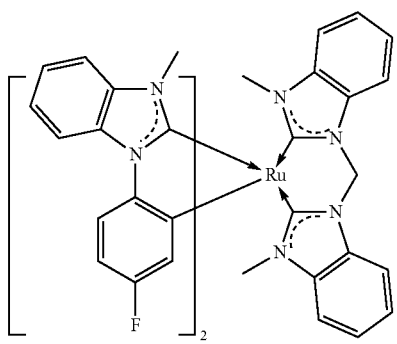

Compound 23

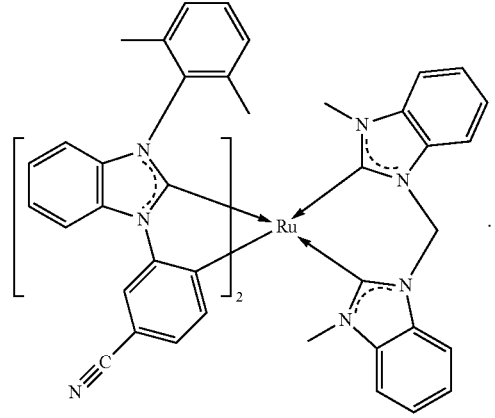

19. The compound of claim 1, wherein the metal complex has the formula XVIII:

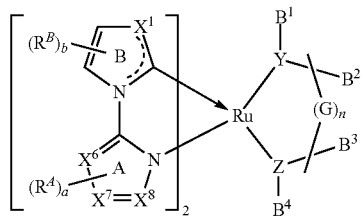

wherein:
X$^6$ is selected from the group C—R$^1$ and N;
X$^7$ is selected from the group C—R$^2$ and N;
X$^8$ is selected from the group C—R$^3$ and N; and wherein R¹, R², and R³ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

20. The compound of claim 19, wherein the metal complex is selected from the group consisting of:

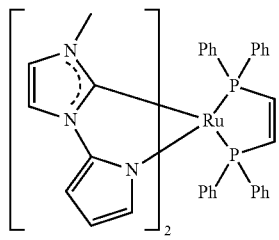

Compound 24

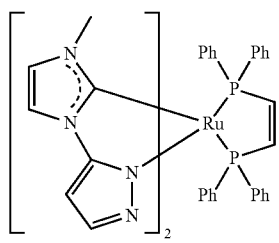

Compound 25

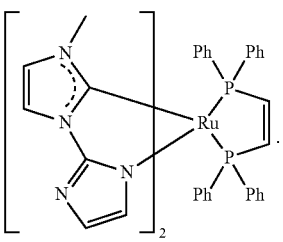

Compound 26

21. The compound of claim 1, wherein the metal complex has the formula XX:

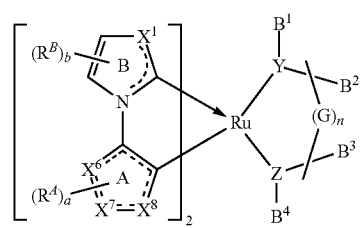

wherein:
X⁶ is selected from the group C—R¹, N, N—R', S, and O;
X⁷ is selected from the group C—R², N, N—R', S, and O;
X⁸ is selected from the group C—R³, N, N—R', S, and O;
wherein the dashed line on ring A represents optional bonds;
wherein at least one of X⁶, X⁷, and X⁸ is a heteroatom or substituted heteroatom; and
wherein R¹, R², and R³ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfonyl, sulfonyl, phosphino, and combinations thereof.

22. The compound of claim 21, wherein the metal complex is selected from the group consisting of:

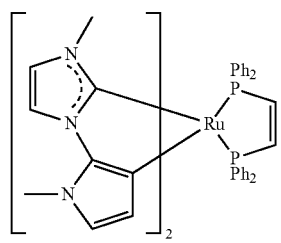

Compound 27

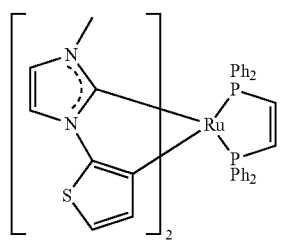

Compound 28

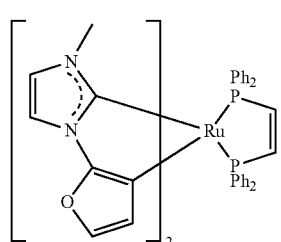

Compound 29

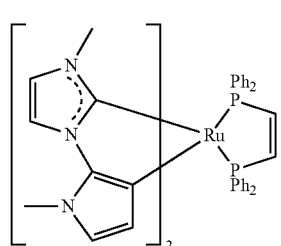

Compound 30

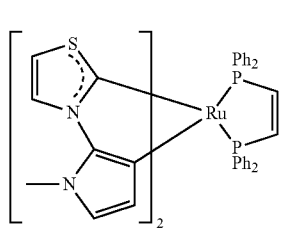

Compound 31

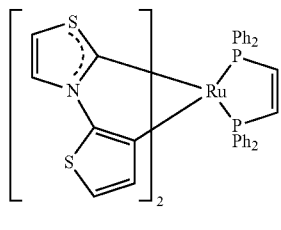

Compound 32

Compound 33

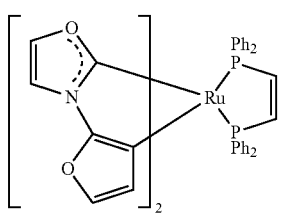

Compound 34

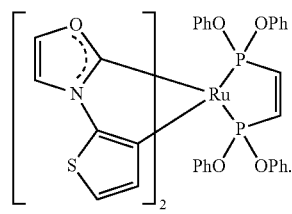

23. The compound of claim 1, wherein at least one of Y and Z is a carbene carbon.

24. A first device comprising an organic light emitting device, further comprising:
an anode;
a cathode; and
an organic layer, disposed between the anode and the cathode, comprising a compound comprising a metal complex having the formula II:

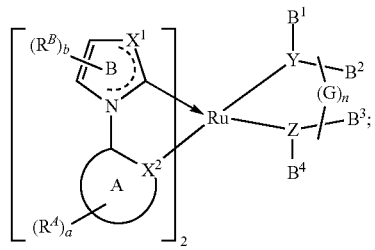

wherein auxiliary ligand

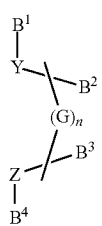

bears no charge;
wherein the Ru bears a +2 charge;
wherein the metal complex has an overall 0 charge;
wherein ring B is connected to the Ru through a carbene bond;
wherein ring A is aromatic and selected from the group consisting of a 5- or 6-membered carbocyclic or heterocyclic group;
each $R^A$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein $R^A$ may be optionally linked to form a ring fused to ring A and wherein the fused ring is optionally substituted;
a is 0 to 4;
$X^1$ is selected from N—R', O, and S;
$X^2$ is selected from C and N;
each $R^B$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein $R^B$ may be optionally linked to form a ring fused to ring B and wherein the fused ring is optionally substituted;
b is 0 to 4;
Y and Z are independently selected from the group consisting of C, and P;
$B^1$, $B^2$, $B^3$, $B^4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
$B^1$ and $B^2$ are optionally linked to form a 5- or 6-membered cyclic group having from 0 to 4 ring heteroatoms, an 8- to 10-membered fused bicyclic group having from 0 to 4 ring heteroatoms, wherein the 5- or 6-membered cyclic group having from 0 to 4 ring heteroatoms, and the 8- to 10-membered fused bicyclic group having from 0 to 4 ring heteroatoms may be optionally substituted with one or more substituents independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl,phosphino, and combinations thereof;
$B^3$ and $B^4$ are optionally linked to form a 5- or 6-membered cyclic group having from 0 to 4 ring heteroatoms, an 8- to 10-membered fused bicyclic group having from 0 to 4 ring heteroatoms, wherein the 5- or 6-membered cyclic group having from 0 to 4 ring heteroatoms, and the 8- to 10-membered fused bicyclic group having from 0 to 4 ring heteroatoms may be optionally substituted with one or more substituents independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
G is selected from the group consisting of alkyl and alkenyl having from 1 to 5 carbon atoms, wherein a first end of G is bonded to Y or $B^2$, and a second end of G is bonded to Z or $B^3$;
n is 0 or 1; wherein when n is 0, G is absent;
wherein R' is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein:
- (a) at least one of Y and Z is a carbene carbon,
- (b) Y is P, Z is P, n=1, and G is alkenyl, or
- (c) Y is P, Z is P, n=1, is alkyl, and $B^1$ is selected from the group consisting of hydrogen, deuterium, halide, alkyl, cycloalkyl, heteroalkyl, arylakyl, alkoxy, aryloxy, amino, silyl, alkenyl, cycloalkenyl, heteroalkenyl, alkynyl, heteroaryl, acyl, carbonyl, carboxylic, acids, ester, nitrile, isonitrile, sulfinyl, sulfonyl, phospino, and combinations thereof.

25. The first device of claim 24, wherein the organic layer is an emissive layer and the compound is an emissive dopant.

26. The first device of claim 25, wherein the organic layer further comprises a host.

27. The first device of claim 24, wherein the first device is a consumer product.

28. The first device of claim 24, wherein the first device is an organic light emitting device.

\* \* \* \* \*

UNITED STATES PATENT AND TRADEMARK OFFICE
CERTIFICATE OF CORRECTION

PATENT NO. : 8,748,011 B2
APPLICATION NO. : 13/033229
DATED : June 10, 2014
INVENTOR(S) : Jui-Yi Tsai It is certified that error appears in the above-identified patent and that said Letters Patent is hereby corrected as shown below:

In the Specification

In column 3, line 45, the last word "sulfanyl" should be -- sulfinyl --
In column 31, line 14, the last word "sulfonyl" should be -- sulfinyl --

In the Claims

In column 107, line 62, of claim 1, "C, N and P" should be -- C and P --
In column 108, line 44, of claim 1, "carbine" should be -- carbene --
In column 108, line 46, of claim 1, ", is alkyl" should be -- , G is alkyl --
In column 108, line 48, of claim 1, "arylakyl" should be -- arylalkyl --
In column 108, line 49, of claim 1, "carboxylic," should be -- carboxylic --
In column 108, line 50, of claim 1, in between the words "isonitrile, sulfinyl" should be -- sulfanyl, --
In column 114, line 22, of claim 9, the first "sulfonyl" should be -- sulfanyl --
In column 120, line 2, of claim 21, the first "sulfonyl" should be -- sulfinyl --
In column 123, line 7, of claim 24, ", is alkyl" should be -- , G is alkyl --
In column 123, line 11, of claim 24, "carboxylic," should be -- carboxylic --
In column 123, line 12, of claim 24, in between the words "isonitrile, sulfinyl" should be -- sulfanyl, --

Signed and Sealed this
Nineteenth Day of August, 2014

Michelle K. Lee
*Deputy Director of the United States Patent and Trademark Office*